US006864270B2

(12) United States Patent
Bergeron, Jr.

(10) Patent No.: US 6,864,270 B2
(45) Date of Patent: Mar. 8, 2005

(54) IRON BINDING AGENTS

(75) Inventor: Raymond J. Bergeron, Jr., Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 10/216,492

(22) Filed: Aug. 8, 2002

(65) Prior Publication Data

US 2003/0083349 A1 May 1, 2003

Related U.S. Application Data

(63) Continuation of application No. 09/723,809, filed on Nov. 28, 2000, now abandoned, which is a continuation of application No. PCT/US99/21726, filed on Sep. 21, 1999.
(60) Provisional application No. 60/101,321, filed on Sep. 21, 1998.

(51) Int. Cl.[7] .................... A61K 31/427; C07D 417/02
(52) U.S. Cl. .................... 514/365; 548/146; 548/200; 548/204; 548/205; 548/215; 548/235; 548/237; 548/311.1; 548/560; 548/565; 548/571; 514/374; 514/385; 514/397; 514/422
(58) Field of Search .................... 514/365, 374, 514/385, 397, 422; 548/146, 200, 204, 205, 215, 235, 237, 311.1, 565, 560, 571

(56) References Cited

U.S. PATENT DOCUMENTS

| 3,274,207 A | 9/1966 | Kollonitsch et al. |
|---|---|---|
| 3,809,754 A | 5/1974 | Bertrand |
| 3,882,110 A | 5/1975 | Clemence et al. |
| 4,367,233 A | 1/1983 | Clark et al. |
| 4,406,905 A | 9/1983 | Zähner et al. |
| 4,457,935 A | 7/1984 | Iwao et al. |
| 4,457,936 A | 7/1984 | Draeger et al. |
| 4,558,059 A | 12/1985 | Kawasaki et al. |
| 4,736,060 A | 4/1988 | Tomuro et al. |
| 4,775,675 A | 10/1988 | Györgydeák et al. |
| 4,902,700 A | 2/1990 | Hayasi et al. |
| 4,914,208 A | 4/1990 | Jakob et al. |
| 5,084,083 A | 1/1992 | Lewis et al. |
| 5,106,992 A | 4/1992 | Magnin et al. |
| 5,169,858 A | 12/1992 | Rubin |
| 5,182,402 A | 1/1993 | Lewis et al. |
| 5,192,781 A | 3/1993 | Bru-Magniez et al. |
| 5,385,922 A | 1/1995 | Bron et al. |
| 5,393,777 A | 2/1995 | Crosa |
| 5,442,073 A | 8/1995 | Eicken et al. |
| 5,614,520 A | 3/1997 | Kondo et al. |
| 5,840,739 A | 11/1998 | Bergeron, Jr. |
| 6,080,764 A | 6/2000 | Chihiro et al. |
| 6,083,966 A | * 7/2000 | Bergeron .................... 514/365 |
| 6,147,070 A | 11/2000 | Facchini |
| 6,159,983 A | 12/2000 | Bergeron, Jr. |
| 6,372,912 B1 | 4/2002 | Döring et al. |
| 6,437,143 B2 | 8/2002 | Moinet et al. |
| 6,521,652 B1 | 2/2003 | Bergeron |
| 6,525,080 B1 | 2/2003 | Bergeron |
| 6,559,315 B1 | 5/2003 | Bergeron |
| 2002/0049316 A1 | 4/2002 | Halbert et al. |

FOREIGN PATENT DOCUMENTS

| DE | 2245 560 A | 3/1974 |
|---|---|---|
| DE | 30 02 989 A1 | 7/1981 |
| EP | 0 214 101 A2 | 8/1986 |
| EP | 0 214 933 A2 | 8/1986 |
| EP | 0 513 379 B1 | 11/1996 |
| FR | 2 247 243 | 5/1975 |
| GB | 1292 170 | 10/1972 |
| GB | 1382887 | 5/1975 |
| WO | WO 94/11367 | 5/1994 |
| WO | WO 97/36885 | 10/1997 |
| WO | WO 99/53039 | 10/1999 |
| WO | WO 00/16763 | 3/2000 |
| WO | WO 01/27119 A2 | 4/2001 |

OTHER PUBLICATIONS

Bergeron, R. J., et al., "The Desferrithiocin Pharmacophore," *J. Med. Chem.*, 37(10): 1411–1417 (1994).
Stahel, Erich, et al., "Iron Chelators: In Vitro Inhibitory Effect on the Liver Stage of Rodent and Human Malaria," *Am. J. Trop. Med. Hyg.*, 39(3):236–240 (1988).
Fritsch, Gerhard, et al., "Plasmodium falciparum: Inhibition in Vitro with Lactoferrin, Desferriferrithiocin, and Desferricrocin," *Experimental Parasitology*, 63:1–9 (1987).
Henry, David W., "Chemotherapeutic Nitroheterocycles. Derivatives of 5–Nitrothiazole–2–carboxaldehyde and 5–Nitrothiazole–2–carboxylic Acid," *J. Med. Chem.*, 12(2):303–306 (1969).
Abstract for Accession No. 80:146142 from Chemical Abstract Database.
Abstract for Accession No. 83:206330 from Chemical Abstract Database.
Bergeron, R.J., "Iron: A Controlling Nutrient Nutrient in Proliferative Processes," *Trends in Biochem. Sci.*, 11; 133–136 (1986).
Bergeron, R.J., et al., "Synthesis and Biological Evaluation of Hydroxamate–Based Iron Chelators," *J. Med. Chem.*, 34: 3182–3187 (1991).
Bergeron, et al., "A Comparison of the Iron–Clearing Properties of 1,2–Dimethyl–3–Hydroxypyrid–4–One 1,2–Diethyl–3–Hydroxypyrid–4–One, and Deferoxamine," *Blood*, 79(7): 1882–1890 (1992).

(List continued on next page.)

Primary Examiner—Charanjit S. Aulakh
(74) Attorney, Agent, or Firm—Hamilton, Brook, Smith & Reynolds, P.C.

(57) ABSTRACT

Composition, article of manufacture for and method of treating malaria in a human having an infestation of Plasmodium protozoans are described. The method comprises administering a therapeutically-effective amount of a compound of formula (I) or (IV), i.e. sufficient quantity to reduce the population of Plasmodium. The composition of the invention is a compound of formula (I) or (IV) with a pharmaceutical excipient. The article of manufacture is the composition in combination with labeling for treating malaria. The substituents are detailed in the specification.

62 Claims, No Drawings

OTHER PUBLICATIONS

Bickel, et al., "Metabolic Properties of Actinomycetes. Ferrioxamine B," *Helv. Chim. Acta*, 43:2129–2138 (1960).

Brittenham, G.M., "Pyridoxal Isonicotinoyl Hydrazone: An Effective Iron–Chelator After Oral Administration," *Semin. Hematol.*, 27(2): 112–116 (1990).

Finch, C.A., et al., "Ferrokinetics in Man," *Medicine (Baltimore)*, 49(1): 17–53 (1970).

Finch, C.A., et al., "Perspectives in Iron Metabolism," *N. Engl. J. Med.*, 306(25): 1520–1528 (1982).

Finch, C.A., and Huebers, H.A., "Iron Metabolism," *Clin. Physiol.Biochem.*, 4: 5–10 (1986).

Ganguly, P.K., and Gupta, B.M., "Antiviral Activity of Isoquinolines Carbazoles and Other Miscellaneous Synthetic Chemicals in Mice," *Indian J. Med. Res.*, 63(10): 1418–1425 (1975).

Grady, R.W., et al., "Rhodotorulic Acid–Investigation of its Potential as an Iron–Chelating Drug," *J. Pharmacol. Exp. Ther.*, 209(3): 342–348 (1979).

Grady, R. W., and Hershko, C., "HBED: A Potential Oral Iron Chelator," *Annals of the N.Y. Acad. Sci.*, 612: 361–368 (1990).

Guterman, S.K., et al., "Feasibility of Enterochelin as an Iron–Chelating Drug: Studies with Human Serum and a Mouse Model System," *Gen. Pharmac.*, 9: 123–127 (1978).

Hallberg, L., "Bioavailability of Dietary Iron in Man," *Ann. Rev. Nutri.*, I:123–147 (1981).

Hoffbrand, A.V., "Transfusion Siderosis and Chelation Therapy," in *Iron in Biochemistry and Medicine, II*, pp. 499–527 (London & New York, 1980).

Kishore, V., et al., "Synthesis of α–Poly–[$N^\epsilon$–(2–aryl–$\Delta^2$–thiazoline–4–carbonyl)L–lysines] with Antiviral Activity," *Indian J. Chem.*, 15B: 255–257 (1977).

Kontoghiorghes, G.J., et al., "1,2–Dimethyl–3–hydroxypyrid–4–one, an Orally Active Chelator for Treatment of Iron Overload," *Lancet*, I: 1294–1295 (1987).

O'Connell, M.J., et al., "The Role of Iron in Ferritin–and Haemosiderin–Mediated Lipid Peroxidation in Liposomes," *Biochem. J.*, 229(1): 135–139 (1985).

Poñka, P., et al., "Mobilization of Iron from Reticulocytes: Identification of Pyridoxal Isonicotinoyl Hydrazone as a New Iron Chelating Agent," *FEBS Lett.*, 97(2): 317–321 (1979).

Raymond, K.N., and Carrano, C.J., "Coordination Chemistry and Microbial Iron Transport," *Acc. Chem. Res.*, 12: 183–190 (1979).

Seligman, P.A., et al., "Molecular Mechanisms of Iron Metabolism," in *The Molecular Basis of Blood Diseases*, pp. 219–244 (W.B. Saunders Company, 1987).

Thomas, C.E., et al., "Ferritin and Superoxide–Dependent Lipid Peroxidation," *J. Biol. Chem.*, 260:3275–3280 (1985).

Uhlir, L.C., et al., "Specific Sequestering Agents for the Actinides. 21. Synthesis and Initial Biological Testing of Octadentate Mixed Catecholate–hydroxypyridinonate Ligands," *J. Med. Chem.*, 36: 504–509 (1993).

Weintraub, L.R., et al., "The Treatment of Hemochromatosis by Phlebotomy," *Med. Clin. of N. America*, 50 (6): 1579–1590 (1966).

Bergeron, R.J., et al. "Evaluation of Desferrithiocin and its Synthetic Analogues as Orally Effective Iron Chelators", *J. of Med. Chem.*, 34(7): 2072–2078 (1991).

Bergeron, R.J., et al. "Effects of C–4 Stereochemistry and C–4' Hydroxylation on the Iron Clearing Efficiency and Toxicity of Desferrithiocin Analogues," *J. Med. Chem.*, 42(13): 2432–2440 (1999).

Jalal, M.A.F., et al. "Structure of Anguibactin, a Unique Plasmid–Related Bacterial Siderophore from the Fish Pathogen *Vibrio Anguillarum*," *J. Am. Chem. Soc.*, 111(1): 292–296 (1989).

Ullmanns Encyclopedia of Industrial Chemistry, $5^{th}$ Edition, vol. A 14, "Ion Exchangers," pp. 446–456.

Bergeron, R.J., et al., "A Comparative Study of the Iron-Clearing Properties of Desferrithiocin Analogues With Desferrioxamine B in a *Cebus* Monkey Model," *Blood*, 81(8):2166–2173, (1993).

Bergeron, R.J., et al., "An Investigation of Desferrithiocin Metabolism," *J. Med. Chem.*, 37(18):2889–2895, (1994).

Bergeron, R.J., et al., "Desazadesmethyldesferrithiocin Analouges as Orally Effective Iron Chelators," *J. Med. Chem.*, 42(1):95–108, (1999).

Bergeron, R.J., et al., "Evaluation of the Desferrithiocin Pharmacophore as a Vector for Hydroxamates," *J. Med. Chem.*, 42(15):2881–2886, (1999).

Bergeron, R.J., et al., "Evaluation of Desferrithiocin and Its Synthetic Analouges as Orally Effective Iron Chelators," *J. Med. Chem.*, 34(7):2072–2078, (1991).

Bergeron, R.J., et al., "Pharmacokinetics of Orally Administered Desferrithiocin Analogs in *Cebus Apella* Primates," *Drug Metabolism and Disposition*, 27(12):1496–1498, (1999).

Bergeron, R.J., et al., "Synthesis and Biological Evaluation of Naphthyldesferrithiocin Iron Chelators," *J. Med. Chem.*, 39(8):1575–1581, (1996).

Bergeron, R.J., et al., "The Origin of the Differences in (R)–and (S)–Desmethyldesferrithiocin: Iron–Clearing Properties," *Annals NY Academy of Sciences*, 850: 202–216 (1998).

Bierer, B.E. and Nathan D.G., "The Effect of Desferrithiocin, an Oral Iron Chelator, on T–Cell Function," *Blood*, 76(10): 2052–2059 (1990).

Cragg, L., et al., "The Iron Chelator L1 Potentiates Oxidative DNA Damage in Iron–Loaded Liver Cells," *Blood*, 92(2): 632–638 (1998).

Dean, R.T. and Nicholson, P., "The Action of Nine Chelators on Iron–Dependent Radical Damage," *Free Rad. Res.*, 20(2): 83–101 (1994).

Re, R., et al., "Antioxidant Activity Applying an Improved ABTS Radical Cation Decolorization Assay," *Free Rad. Biol. Med.*, 26(9/10): 1231–1237 (1999).

* cited by examiner

IRON BINDING AGENTS

RELATED APPLICATION(S)

This application is a continuation of U.S. application Ser. No. 09/723,809, filed Nov. 28, 2000, now abandoned which is a continuation of PCT/US99/21726, filed Sep. 21, 1999, which claims the benefit of U.S. Provisional Application Ser. No.: 60/101,321, filed Sep. 21, 1998, the entire teachings of which are incorporated herein by reference.

GOVERNMENT SUPPORT

The invention was supported, in whole or in part, by Grant Nos. 3203522-12, RO1HL42817 and RO1DK49108 from the National Institutes of Health (NIH). The Government has certain rights in the invention.

TECHNICAL FIELD

This invention relates to the treatment of malaria with pharmaceutical compositions comprising certain compounds related to desferrithiocin. The compositions are particularly useful for the treatment of Plasmodium falciparum malaria.

BACKGROUND OF THE INVENTION

Malaria is one of the oldest and most widespread infectious diseases plaguing mankind. Among human parasitic diseases, it is the most deadly. It is endemic in developing countries and infects over 500 million people each year, killing over 2.7 million of them. Thanks in part to new treatments for the disease, during the middle part of the 20$^{th}$ century the incidence of malaria was decreasing each year. In recent years, however, cases of malaria have dramatically increased worldwide including thousands of cases in the United States. This increase is due in part to the emergence of drug resistant strains of the disease.

Malaria is caused by eukaryotic protozoans of the genus Plasmodium. Of the 100 species of Plasmodium, four are known to cause malaria in humans. Three of these species, Plasmodium vivax, Plasmodium malariae, and Plasmodium ovale cause relatively benign forms of the disease. The fourth species, Plasmodium falciparum, is malignant and the most lethal, being responsible for the majority of deaths from malaria world wide.

P. falciparum malaria is introduced into human hosts through a bite from the female Anopheles mosquito. An infected mosquito will bite a human and inject a small amount of saliva with anticoagulant and haploid sporozoites of the P. falciparum parasite. The sporozoites enter the circulatory system and reach the liver in an hour or so. In the liver they will enter hepatic parenchymal cells in what is called the exoerythrocytic stage of the disease cycle. During the 5–7 days of this stage, they will undergo multiple asexual fission, schizogony, multiplying 30,000 to 40,000-fold, and produce merozoites.

As merozoites, they will leave the liver, reenter the bloodstream, invade erythrocytes (red blood cells), and begin the erythrocytic stage. Once inside the erythrocyte, P. falciparum begins to enlarge as an uninucleate trophozoite. Over another 1–3 days, this trophozoite will divide asexually to produce a schizont containing 6–24 nuclei. The schizont will divide and produce mononucleated merozoites. This causes the erythrocyte to lyse and release merozoites into the blood stream to infect other erythrocytes.

Some merozoites will differentiate into macrogametocytes and microgametocytes, which do not cause erythrocytes to lyse. These male and female sexual forms can be ingested by a mosquito, in which they will be fertilized to form zygotes which will produce sporozoites in the mosquito's salivary glands to permit reinfection of other human hosts.

Malaria is asymptomatic until the erythrocytic stage when the synchronized release of merozoites and debris from erythrocytes into the circulation causes the classical malarial signs and symptoms. These include paroxysms (spasms and convulsions), high fever, rigors (stiffness and chills), profuse sweating, vomiting, anemia, headache, muscle pains, spleen enlargement, and hypoglycemia. Since the release of merozoites occurs every 48 hours or so in P. falciparum malaria, the symptoms are tertian, occurring every third day. In between merozoite releases of the erythrocytic stage, a human host will feel normal and be asymptomatic.

The most severe consequence of P. falciparum malaria is the aggregation, clumping, or sludging of infected erythrocytes, including adherence to blood vessel walls. Depending on the site of the sludging, life threatening effects can occur due to the restriction of blood flow to vital organs. These include encephalopathy for cerebral malaria, pulmonary edema, acute renal failure, severe intravascular hemolysis, and hemoglobinuria. The vast majority of deaths caused by P. falciparum malaria are due to these effects.

Traditional treatments of malaria are based on either the control of mosquito populations, vaccines, or chemotherapy. For chemotherapy, drugs are generally targeted at specific stages of the disease. Such drugs include tissue schizonticides, such as chloroquine, used to eradicate the exoerythrocytic stage in the liver; blood schizonticides, such as chloroquine, folate antagonists, and the 8-aminoquinolines referred to as pyrimethamine, primaquine, and pamaquine, used to destroy the erythrocytic stage; gametocytocides, such as 4-aminoquinolines, used to kill gametocytes; and sporonticides used to kill sporozoites.

In recent years, the most effective treatment for malaria, particularly for P. falciparum malaria, has been the 4-aminoquinoline, chloroquine. This drug of choice to treat the disease is active against the erythrocytic form of P. vivax and P. falciparum. Chloroquine acts as a blood schizonticidal agent and rarely produces serious side effects. It inhibits nucleic acid and protein synthesis in protozoal cells. It is used both for the treatment of acute onset malignant tertian P. falciparum malaria and prophylactically.

It has been the prophylactic use of many chemotherapeutic treatments for malaria that has led to the emergence of drug resistant strains of Plasmodium species that cause malaria. Plasmodium resistance to chloroquine has now become widespread and is a serious problem. This has lead to the development of alternative chemotherapeutic agents.

Compounds to emerge include folate antagonists, including sulfones and sulfonamides, such as dapsone, sulfadoxine, sulfadiazine, and sulfalene; primines, and biguanides. These compounds compete with p-aminobenzoic acid (PABA), interfere with synthesis of tetrahydrofolic acid, and act as blood schizonticides. However, their effective doses can be extremely toxic and Plasmodium can readily develop resistance to these drugs.

The ability of Plasmodium species to develop resistance to drugs coupled with the undesirable side effects of such drugs has resulted in the constant development of new treatments. Thus, there are numerous compounds currently available, or in development, for the treatment of malaria.

Antiprotozoal compounds that can be or have been used as treatments against malaria may be found by referring to

*Goodman and Gilman's The Pharmacological Basis of Therapeutics*, Eighth Edition, McGraw-Hill, Inc. (1993), Chapter 41, pages 978–998.

As indicated above, strains of *P. falciparum* that are resistant to one or more of the available treatments for malaria are ubiquitous today. As new compounds to attack the parasite directly are developed, a new resistant strain emerges. Additionally, the continued undesirable side effects of available drugs present problems. This is particularly true when multiple drugs must be administered to battle concurrent infections of more than one Plasmodium species, which have become quite common. Thus, not only are yet more alternative chemotherapeutic treatments for malaria desired, particularly for *P. falciparum* malaria, but also entirely new mechanisms of action for the eradication of the Plasmodium parasite are desired. Such mechanisms may make it more difficult for strains of the parasite to emerge that are resistant to these new drugs.

OBJECTS OF THE INVENTION

One object of this invention is to provide a new family of antimalarials which are particularly active against *P. falciparum* and yet have relatively low toxicity over the treatment regimen.

Another object of this invention is to provide a new method for treating malaria using the new family of antimalarials.

Another object of this invention is to provide a novel method for the treatment of *P. falciparum* malaria, particularly in strains of *P. falciparum* that are resistant to traditional chemotherapeutic antimalarial agents.

Other objects will become apparent to one of ordinary skill in the art upon reading the following disclosure.

SUMMARY OF THE INVENTION

One aspect of the invention is an antimalarial composition comprising a compound, represented by formula (I), in combination with a pharmaceutically acceptable excipient. The formula is

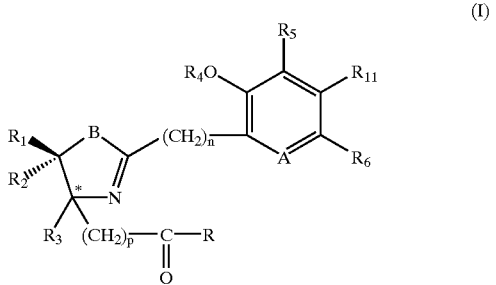

(I)

In the formula (I), the substituents are defined as follows:

R is OH, $OR_7$, or $N(OH)R_8$;

$R_1$ is H, $CH_3$ or an available electron;

$R_2$ is H, $CH_3$ or an available electron;

$R_3$ is H, $CH_3$ (as the (R) or (S) configuration) or an available electron and together with either $R_1$ or $R_2$ when one is an available electron, forms a double bond with the $R_1/R_2$ carbon;

$R_4$ is H, acyl of 1–4 carbons or alkyl of 1–4 carbons;

$R_5$ is H, OH, O-acyl of 1–4 carbons, O-alkyl of 1–4 carbons, or $(CH_2)_a(R_{10})_b(CH_2)_aR_{10}(CH_2)_a(R_{10})_bX$;

$R_6$ is H, OH, alkyl of 1–6 carbons, a halogen, $(CH_2)_aR_{10}(CH_2)_rR_{10}Y$, or is —C≡C—C≡C—, which, together with $R_{11}$ when $R_{11}$ is an available electron, forms a fused ring system as follows:

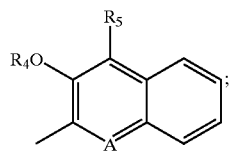

$R_7$ is alkyl of one to four carbons or optionally substituted benzyl;

$R_8$ is H, alkyl of one to four carbons, optionally substituted benzyl,

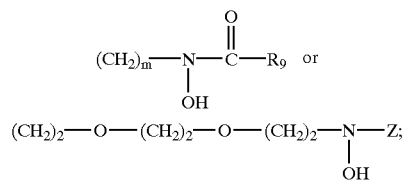

$R_9$ is H, alkyl of one to four carbons or optionally substituted benzyl;

$R_{10}$ is O or $CH_2$;

$R_{11}$ is H, OH, O-acyl of 1–4 carbons, O-alkyl of 1–4 carbons or an available electron;

A is N, CH or COH;

B is S, O, N, $CH_2$ or $CH_2S$;

a is 2 or 3;

b is 0 or 1;

m is an integer from 1 to 8;

n is 0 or 1;

p is 0, 1 or 2;

r is 2 or 3;

X is

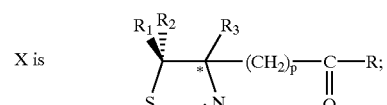

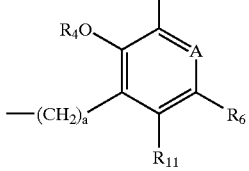

Y is

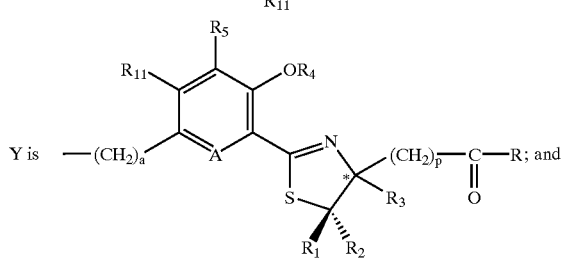

-continued

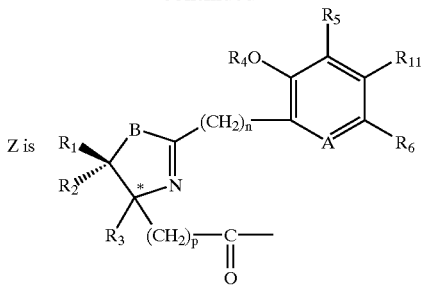

For each of X, Y and Z, each of the substituents shown is defined above. Also included is a compound of formula (I) where the ring containing the B and N moieties is fully reduced and contains no double bonds. It is to be understood that for each of the formulas in this application, included are pharmaceutically-acceptable salts of the compound represented by formula (I) and their individual stereoisomers and mixtures thereof. Preferred aspects are discussed hereinafter in the Detailed Description.

Another aspect of the invention is a compound of the formula (I) wherein:

R is $N(OH)R_8$;

each of $R_1$, $R_2$ and $R_3$ is H or $CH_3$;

$R_4$ is H, acyl of 1–4 carbons or alkyl of 1–4 carbons;

$R_5$ is H, OH, O-acyl of 1–4 carbons or O-alkyl of 1–4 carbons;

$R_6$ is H, OH, alkyl of 1–6 carbons or halogen;

$R_8$ is

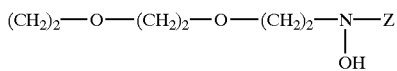

$R_{11}$ is H, OH, O-acyl of 1–4 carbons or O-alkyl of 1–4 carbons;

A is N or CH;

B is S, O, N, $CH_2$ or $CH_2S$;

n and p each is 0;

Z is

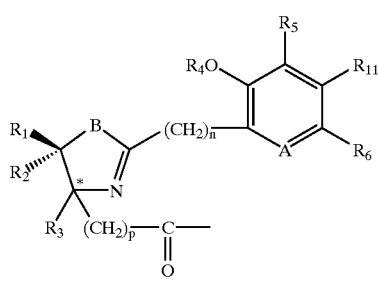

wherein each of the substituents shown is described above.

Another aspect of this invention is a compound of the formula (I) wherein:

R is OH, $OR_7$ or $N(OH)R_8$;

each of $R_1$, $R_2$ and $R_3$ is H or $CH_3$;

$R_4$ is H, acyl of 1–4 carbons or alkyl of 1–4 carbons;

$R_5$ is $(CH_2)_a(R_{10})_b(CH_2)_aR_{10}(CH_2)_a(R_{10})_bX$;

$R_6$ is H, OH, alkyl of 1–6 carbons or halogen;

$R_7$ is alkyl of 1–4 carbons or optionally substituted benzyl;

$R_8$ is H, alkyl of 1–4 carbons, optionally substituted benzyl or $(CH_2)_mN(OH)C(O)R_9$ $R_9$ is H, alkyl of 1–4 carbons or optionally substituted benzyl.

$R_{10}$ is O or $CH_2$;

$R_{11}$ is H, OH, O-acyl of 1–4 carbons or O-alkyl of 1–4 carbons;

A is N or CH;

B is S, O, N, $CH_2$ or $CH_2S$;

a is 2 or 3;

b is 0 or 1;

n and p each is 0;

r is 2 or 3; and

X is

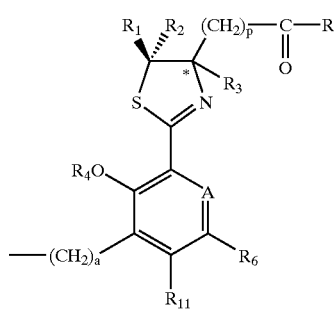

wherein each of the substituents shown is described above,

Another aspect of this invention is a compound of the formula (I) wherein:

R is OH, $OR_7$ or $N(OH)R_8$;

each of $R_1$, $R_2$ and $R_3$ is H or $CH_3$;

$R_4$ is H, acyl of 1–4 carbons or alkyl of 1–4 carbons;

$R_5$ is H, OH, O-acyl of 1–4 carbons or O-alkyl of 1–4 carbons;

$R_6$ is $(CH_2)_aR_{10}(CH_2)_rR_{10}Y$;

$R_7$ is alkyl of 1–4 carbons or optionally substituted benzyl;

$R_8$ is H, alkyl of 1–4 carbons, optionally substituted benzyl or $(CH_2)_mN(OH)C(O)R_9$ $R_9$ is H, alkyl of 1–4 carbons or optionally substituted benzyl;

$R_{10}$ is O or $CH_2$;

$R_{11}$ is H, OH, O-acyl of 1–4 carbons or O-alkyl of 1–4 carbons;

A is N or CH;

B is S, O, N, $CH_2$ or $CH_2S$;

a is 2 or 3;

b is 0 or 1;

n and p each is 0;

r is 2 or 3;

Y is

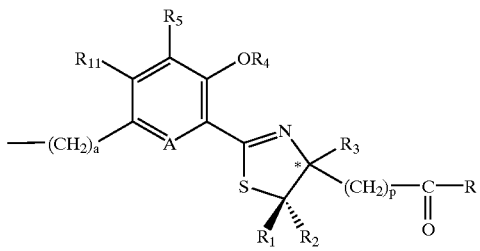

wherein each of the substituents shown is described above.

Another aspect of the invention is a compound of the formula:

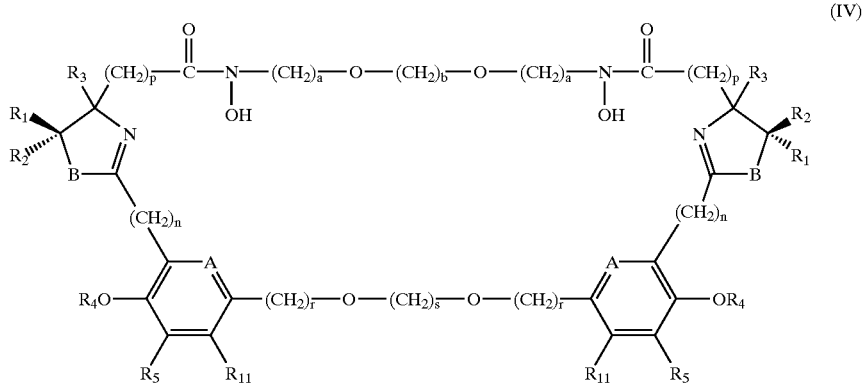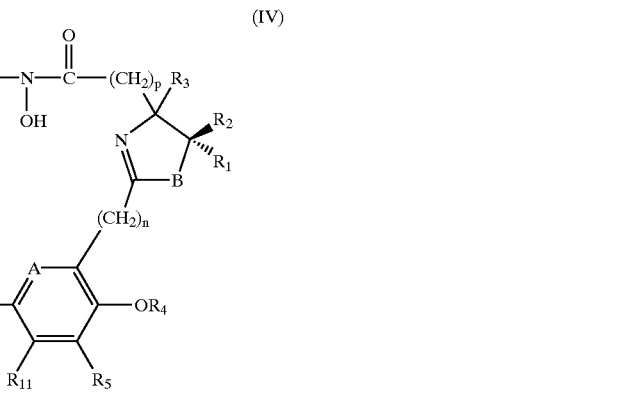

wherein:
- $R_1$ is H or $CH_3$;
- $R_2$ is H or $CH_3$;
- $R_3$ is H or $CH_3$;
- $R_4$ is H, acyl of 1–4 carbons or alkyl of 1–4 carbons;
- $R_5$ is H, OH, O-acyl of 1–4 carbons or O-alkyl of 1–4 carbons;
- $R_{11}$ is H, OH, O-acyl of 1–4 carbons or O-alkyl of 1–4 carbons;
- A is N or CH;
- B is S, O, N, $CH_2$ or $CH_2S$;
- a is 1, 2 or 3;
- b is an integer from 2 to 8;
- n is 0 or 1;
- p is 0, 1 or 2;
- r is 1, 2 or 3; and
- s is 1, 2 or 3.

Another aspect of the invention is a compound of formula (I) wherein:
- R is OH, $OR_7$ or $N(OH)R_8$;
- $R_1$, $R_2$ and $R_3$ are H or $CH_3$;
- $R_4$ is H, acyl of 1–4 carbons or alkyl of 1–4 carbons;
- $R_5$ is H, OH, O-acyl of 1–4 carbons or O-alkyl of 1–4 carbons;
- $R_6$ is hexyl;
- $R_7$ is alkyl of 1–4 carbons or optionally substituted benzyl;
- $R_8$ is H, alkyl of 1–4 carbons, optionally substituted benzyl or $(CH_2)_m N(OH)C(O)R_9$;
- $R_9$ is H, alkyl of 1–4 carbons or optionally substituted benzyl;
- $R_{11}$ is H, OH, O-acyl of 1–4 carbons or O-alkyl of 1–4 carbons;
- A is N or CH;
- B is S, O, N, $CH_2$ or $CH_2S$;
- m is an integer from 1 to 8;
- n is 0 or 1; and
- p is 0, 1 or 2.

Another aspect of the invention is a method of treating malaria in an animal, which method comprises administering an antimalarial amount of compound set forth in this summary of the invention.

Another aspect of the invention is a method of preparing a composition useful for treating malaria, which method comprises combining the compound set forth above in this summary of the invention with a pharmaceutically acceptable excipient.

Another aspect of the invention is a pharmaceutical composition designed for treating malaria. The composition comprises a compound of formula (I) or formula (IV) in combination with a pharmaceutically acceptable excipient.

Another aspect of the invention is an article of manufacture that comprises a pharmaceutical composition having a compound represented by formula (I) or (IV) with a pharmaceutically acceptable excipient in association with labeling describing the use of the composition for treating malaria.

DETAILED DESCRIPTION AND PRESENTLY PREFERRED EMBODIMENTS

The present invention is based on the discovery that iron-chelating compounds of the above formulas are effective, i.a., against *Plasmodium falciparum*. Such compounds deprive this parasite of much needed iron for its metabolic processes. The compounds can be administered to humans in doses wholly unsuitable for chronic therapy due to the brief dosing interval required for the treatment of malaria.

Applicant has identified compounds for the eradication of the Plasmodium parasite that is targeted at the regulation of cellular iron metabolism. Iron, the fourth most abundant element in the earth's crust, is also ubiquitous in all life forms. Eukaryotic microorganisms require iron to sustain life. Iron is critical for use by cytochromes and as a cofactor for enzymes in electron-carrying proteins, for example.

While iron chelators, such as desferrithiocin (DFT) have been used for the treatment of tranfusion-induced iron overload in β-thalassemia and aplastic anemia, such compounds were not contemplated for use in the treatment of malaria prior to Applicant's invention. DFT is a superior iron chelating agent. It is well absorbed orally and is highly efficient at complexing with iron ions. However, it can be highly nephrotoxic when used over time. This is particularly problematic, since chelation therapy is a lifetime treatment of transfusion induced iron-overload in patients suffering with β-thalassemia. The chronic toxicity of DFT has resulted in its complete abandonment for treatment of chronic iron overload, despite its high efficiency as an iron chelator.

It has been discovered that, in part because treatment of malaria with compounds disclosed in this application would only require a brief dosing interval, patients would escape the chronic toxicity associated with the historical uses of DFT and related compounds. In fact, the new dimension of toxicity of siderophores for the treatment of malaria permits the development of new DFT analogs that are even more efficient iron chelators yet still provide manageable toxicity over the shorter course of treatment for this disease. Thus, analogs of DFT that would not be acceptable for traditional iron chelation therapy may become viable candidates for the treatment of malaria, particularly for deadly P. falciparum malaria.

X-ray crystallography studies of the desferrithiocin pharmacophore have indicated that the three ligating centers, i.e., the aromatic hydroxyl, the thiazoline nitrogen, and the carboxyl group, are important to the compound's iron clearing capabilities. Any structural modifications to the above functional groups should affect the ability of DFT to coordinate with iron. An understanding of how to minimize the toxicity of analogs of DFT, however, has remained unclear. The present invention provides a range of compounds that strike a balance between optimal iron chelating ability and minimum toxicity.

COMPOUNDS USEFUL IN THE INVENTION

"Alkyl" means a fully saturated hydrocarbon radical having the number of carbon atoms indicated. For example, alkyl of 1 to 6 includes, e.g., methyl, ethyl, n-propyl, i-propyl, n-butyl, i-butyl, t-butyl, n-pentyl, amyl, n-hexyl, and the like.

"Acyl" means a radical of the formula

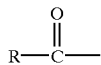

where R is a hydrocarbon such as alkyl. An acyl of one to four carbons would include those where R is an alkyl of one to three carbons. These would include for example acetyl ($CH_3$—C(O)—), propionyl ($CH_3$—$CH_2$—C(O)—) or butyryl ($CH_3(CH_2)_2C(O)$—) or isobutyryl.

"Hexyl" means an alkyl of 6 carbons of any isomeric configuration, such as n-hexyl, 1-methylpentyl, 1-ethylbutyl, 1,1-dimethylbutyl and the like. The n-hexyl radical is preferred.

"Optionally substituted benzyl" is a benzyl group, ie., phenylmethyl ($PhCH_2$—), that is either unsubstituted or substituted with one to four carbons, hydroxy, alkoxy of one to four carbons, halogen, acyl of one to four carbons, and the like.

Compounds useful for preparing the composition and article of manufacture of this invention and for treating malaria are broadly defined as compounds represented by Formulas (I) and (IV). Included within the scope of the invention are the compounds per se, pharmaceutically acceptable salts of the compounds, and stereoisomeric (e.g. enantiomers, diastereomers) variations of the compounds.

Formula I is the following:

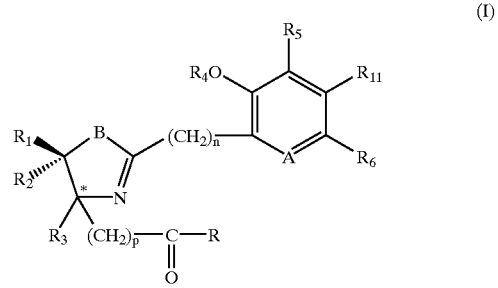

(I)

The substituents of formula (I) are defined as follows:

R is OH, $OR_7$, or $N(OH)R_8$;

$R_1$ is H, $CH_3$ or an available electron;

$R_2$ is H, $CH_3$ or an available electron;

$R_3$ is H, $CH_3$ at the (R) or (S) configuration, or an available electron and together with either $R_1$ or $R_2$ when one is an available electron, forms a double bond with the $R_1/R_2$ carbon;

$R_4$ is H, acyl of 1–4 carbons or alkyl of 1–4 carbons;

$R_5$ is H, OH, O-acyl of 1–4 carbons, O-alkyl of 1–4 carbons, or $(CH_2)_a(R_{10})_b(CH_2)_aR_{10}(CH_2)_a(R_{10})_bX$;

$R_6$ is H, OH, alkyl of 1–6 carbons, a halogen, $(CH_2)_aR_{10}(CH_2)_rR_{10}Y$, or is —C=C—C=C—, which, together with $R_{11}$ when $R_{11}$ is an available electron, forms a fused ring system as follows:

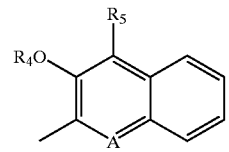

$R_7$ is alkyl of one to four carbons or optionally substituted benzyl;

$R_8$ is H, alkyl of one to four carbons, optionally substituted benzyl,

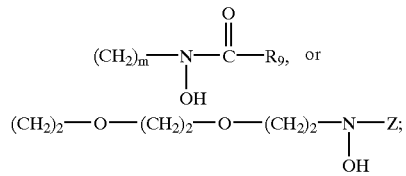

$R_9$ is H, alkyl of one to four carbons or optionally substituted benzyl;

$R_{10}$ is O or $CH_2$;

$R_{11}$, is H, OH, O-acyl of 1–4 carbons, O-alkyl of 1–4 carbons or an available electron;

A is N, CH or COH;

B is S, O, N, $CH_2$ or $CH_2S$;

a is 2 or 3;

b is 0 or 1;

m is an integer from 1 to 8;

n is 0 or 1;
p is 0, 1 or 2;
r is 2 or 3;

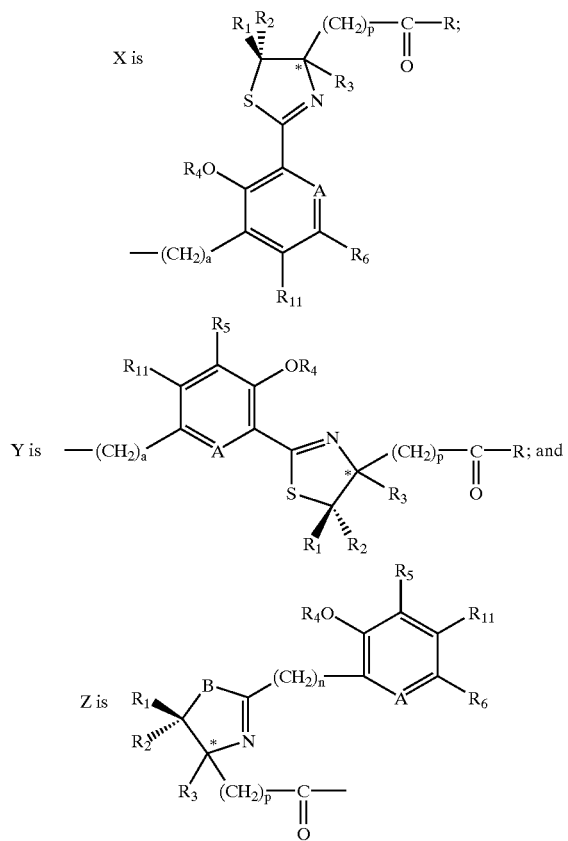

For each of X, Y, and Z, each of the substituents shown is defined above.

Also included is a compound of formula (I) where the ring containing the B and N moieties is fully reduced and contains no double bonds. These compounds can be subdivided into those where A is N (i.e. pyridyl derivatives) and those where A is CH (i.e. benzene derivatives).

When A is N, those compounds where B is S and each of n and p is 0 (thiazolines) are particulary useful. Preferred are compounds where each of $R_1$, $R_2$ and $R_3$ is H or $CH_3$;
each of $R_5$ and $R_{11}$ is H, OH, O-acyl of 1–4 carbons or O-alkyl of 1–4 carbons,
$R_6$ is H, OH, alkyl of 1–6 carbons or a halogen, and
$R_7$ is alkyl of 1–4 carbons.

Of this subgroup, compounds where $R_4$ is H and R is OH are preferred. A representative compound is one where each of $R_1$, $R_2$, $R_3$, $R_5$, $R_6$ and $R_{11}$ is H (compound 2 in Table I).

In the instance where R is $N(OH)R_8$, a compound where $R_8$ is methyl is useful. A representative compound is one wherein each of $R_1$, $R_2$, $R_3$, $R_5$, $R_6$ and $R_{11}$ is H (Compound 22 in Table I); When $R_8$ is $(CH_2)_mN(OH)COR_9$, a representative compound is that wherein each of $R_1$, $R_2$, $R_3$, $R_5$, $R_6$ and $R_{11}$ is H; m is 5; and $R_9$ is $CH_3$. (Compound 23 in Table 1); When $R_8$ is $(CH_2)_2O(CH_2)_2O(CH_2)_2N(OH)Z$, a representative compound is one where each of $R_1$, $R_2$, $R_3$, $R_5$, $R_6$ and $R_{11}$ is H. (Compound 25 in Table I).

When A is CH, those compounds wherein B is S, and n and p each is 0 (thiazolines) are particularly useful. Preferred is the subgroup wherein each of $R_1$, $R_2$, $R_3$ and $R_4$ is H or $CH_3$,
each of $R_5$ and $R_{11}$ is H, OH, O-acyl of 1–4 carbons or O-alkyl of 1–4 carbons,
$R_6$ is H, OH, alkyl of 1–6 carbons or a halogen, and
$R_7$ is alkyl of 1–4 carbons.

Of this subgroup, compounds where $R_4$ is H and R is OH are of particular interest.

When $R_{11}$ is H, representative compounds include those wherein each of $R_1$, $R_2$, $R_3$, $R_5$ and $R_6$ is H (Compound 3 in Table I); wherein $R_6$ is OH and each of $R_1$, $R_2$, $R_3$ and $R_5$ is H (Compound 29 in Table I); wherein $R_6$ is F and each of $R_1$, $R_2$, $R_3$ and $R_5$ are H (Compound 29a in Table I); and wherein $R_6$ is OH, $R_3$ is $CH_3$, and $R_1$, $R_2$, and $R_5$ is H (Compound 33 in Table I). A representative compound where $R_{11}$ is OH, is one wherein each of $R_1$, $R_2$, $R_3$, $R_5$ and $R_6$ is H. (Compound 5 in Table I). A compound where $R_{11}$ is OH, $R_6$ is hexyl and each of $R_1$, $R_2$, $R_3$ and $R_5$ is H is also of particular interest. Other compounds where $R_{11}$ is OH, include one, wherein $R_6$ is OH and each of $R_1$, $R_2$, $R_3$ and $R_5$ is H. (Compound 35 in Table I) and one, wherein $R_6$ is OH, $R_3$ is $CH_3$, and each of $R_1$, $R_2$ and $R_5$ is H. (Compound 38 in Table I).

Compounds in which $R_5$ is $(CH_2)_a(R_{10})_b(CH_2)_aR_{10}$ $(CH_2)_a(R_{10})_bX$, can be considered to be a "dimer" in that there are two essentially similar parts of the molecule. A particularly interesting dimer is one wherein $R_{11}$ is OH, and each of $R_1$ and $R_2$ is H, especially wherein a is 2 and each of $R_3$ and $R_6$ is H. Representative compounds are those where $R_{10}$ is $CH_2$ and b is 0 (Compound 40 in Table I); wherein $R_{10}$ is $CH_2$ and b is 1 (Compound 41 in Table I); wherein $R_{10}$ is O and b is 0 (Compound 42 in Table I); and wherein $R_{10}$ is O and b is 1 (Compound 43 in Table I).

Another "dimer" is represented by Formula (I), wherein $R_6$ is $(CH_2)_aR_{10}(CH_2)_rR_{10}Y$. Preferred in this dimer subgroup are compounds and wherein $R_{11}$ is OH, and each of $R_1$ and $R_2$ is H and wherein a is 3, and each of $R_3$ and $R_5$ is H. Of this preferred dimer subgroup, compounds of special interest are those wherein $R_{10}$ is $CH_2$ and r is 2 (Compound 44 in Table I); wherein $R_{10}$ is $CH_2$ and r is 3 (Compound 45 in Table I); wherein $R_{10}$ is O and r is 2 (Compound 46 in Table I); and wherein $R_{10}$ is O and r is 3 (Compound 47 in Table I).

Of the general benzene/thiazoline compounds, those wherein R is $N(OH)R_8$ (i.e. hydroxamates) are of significant interest. Of these hydroxamates, those dimers wherein $R_6$ is $(CH_2)_aR_{10}(CH_2)_rR_{10}Y$ are of particular interest, especially those wherein $R_{11}$ is OH, and each of $R_1$ and $R_2$ is H and wherein a is 3 and each of $R_3$ and $R_5$ is H. A representative compound is one wherein $R_8$ is $CH_3$, $R_{10}$ is O and r is 3. (Compound 48 in Table I). Another representative hydroxamate dimer is one wherein $R_8$ is $(CH_2)_2O(CH_2)_2O$ $(CH_2)_2N(OH)Z$. The dimers wherein $R_{11}$ is OH and each of $R_1$ and $R_2$ is H are of significant interest. A representative compound is one wherein each of $R_3$, $R_5$ and $R_6$ is H (Compound 50 in Table I).

Another useful compound is one of formula (IV), namely.

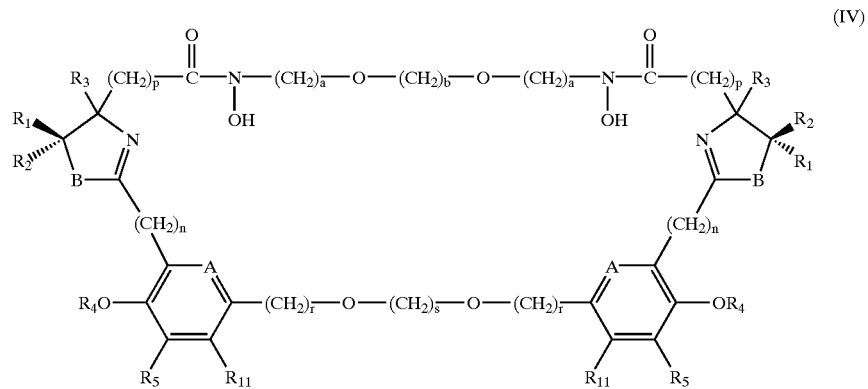

In formula (IV), the substituents are defined as follows:
$R_1$ is H or $CH_3$;
$R_2$ is H or $CH_3$;
$R_3$ is H or $CH_3$;
$R_4$ is H, acyl of 1–4 carbons or alkyl of 1–4 carbons;
$R_5$ is H, OH, O-acyl of 1–4 carbons or O-alkyl of 1–4 carbons;
$R_{11}$ is H, OH, O-acyl of 1–4 carbons or O-alkyl of 1–4 carbons;
A is N or CH;
B is S, O, N, $CH_2$ or $CH_2S$;
a is 1, 2 or 3;
b is an integer from 2 to 8;
n is 0 or 1;
p is 0, 1 or 2;
r is 1, 2 or 3; and
s is 1, 2 or 3.

Those compounds of particular interest are those wherein A is CH, especially wherein B is S with $R_4$ being H and further wherein $R_{11}$ is OH, $R_1$, $R_2$ and $R_5$ are H, and each of n and p is 0. A representative compound is one wherein each of r and s is 3, a is 2, and b is 2 (Compound 49 in Table I).

Compounds that are particularly useful in the composition, the method of treatment and the article of manufacture of this invention are set forth in Table I. In Table I, the left hand, vertical column lists the substituent of formula (I), (i.e. A, $R_1$, a, etc) while the top, horizontal row gives the compound number (i.e. 1–51). The compound designated as #8 is of particular interest.

TABLE I

| Cpd | 1 | 2 | 3 | 4 | 5 | 6 | 7 | 8 | 9 | 11 | 12 | 14 | 15 | 16 | 17 |
|---|---|---|---|---|---|---|---|---|---|---|---|---|---|---|---|
| A | N | N | CH | CH | CH | CH | CH | CH | CH | CH | CH | N | CH | CH | CH |
| B | S | S | S | S | S | S | S | S | S | N | $CH_2$ | $CH_2S$ | S | S | S |
| R | OH | OH | OH | OH | OH | OH | OH | OH | OH | OH | OH | OH | OH | OH | OH |
| R1 | H | H | H | H | H | H | H | $CH_3$ | H | H | H | H | H | H | H |
| R2 | H | H | H | H | H | H | H | $CH_3$ | H | H | H | H | H | H | H |
| R3 | $CH_3$ | H | H | H | H | H | H | H | $CH_3$ | H | H | H | H | H | H |
| R4 | H | H | H | H | H | H | H | H | H | H | H | H | H | H | H |
| R5 | H | H | H | OH | H | $OCH_3$ | H | H | H | H | H | H | H | H | H |
| R6 | H | H | H | H | H | H | H | H | H | H | $CH_3$ | H | H | H | H |
| R7 | — | — | — | — | — | — | — | — | — | — | — | — | — | — | — |
| R8 | — | — | — | — | — | — | — | — | — | — | — | — | — | — | — |
| R9 | — | — | — | — | — | — | — | — | — | — | — | — | — | — | — |
| R10 | — | — | — | — | — | — | — | — | — | — | — | — | — | — | — |
| R11 | H | H | H | H | OH | H | $CO_2H$ | H | H | H | H | H | H | H | H |
| a | — | — | — | — | — | — | — | — | — | — | — | — | — | — | — |
| b | — | — | — | — | — | — | — | — | — | — | — | — | — | — | — |
| m | — | — | — | — | — | — | — | — | — | — | — | — | — | — | — |
| n | 0 | 0 | 0 | 0 | 0 | 0 | 0 | 0 | 0 | 0 | 0 | 0 | 1 | 0 | 0 |
| p | 0 | 0 | 0 | 0 | 0 | 0 | 0 | 0 | 0 | 0 | 0 | 0 | 0 | 1 | 2 |
| r | — | — | — | — | — | — | — | — | — | — | — | — | — | — | — |

| Cpd | 18, 19 | 20, 21 | 22 | 23 | 24 | 25 | 28 | 29 | 29a | 33 |
|---|---|---|---|---|---|---|---|---|---|---|
| A | CH | N | N | N | N | N | CH | CH | CH | CH |
| B | S | S | S | S | S | S | S | S | S | S |
| R | OH | OH | $N(OH)R_8$ | $N(OH)R_8$ | $N(OH)R_8$ | $N(OH)R_8$ | OH | OH | OH | OH |
| R1 | H | H | H | H | H | H | H | H | H | H |
| R2 | H | H | H | H | H | H | H | H | H | H |
| R3 | H | H | H | H | H | H | $CH_3$ | H | H | $CH_3$ |

TABLE I-continued

| | | | | | | | | | | |
|---|---|---|---|---|---|---|---|---|---|---|
| R4 | H | H | H | H | H | H | H | H | H | H |
| R5 | H | H | H | H | H | H | H | H | H | H |
| R6 | —C=C—C=C— | —C=C—C=C— | H | H | H | H | H | OH | F | OH |
| R7 | — | — | — | — | — | — | — | — | — | — |
| R8 | — | — | $CH_3$ | $(CH_2)_m$NOHCOR$_9$ | benzyl | Z monomer (1) | — | — | — | — |
| R9 | — | — | — | $CH_3$ | — | — | — | — | — | — |
| R10 | — | — | — | — | — | — | — | — | — | — |
| R11 | bond | bond | H | H | H | H | OH | H | H | H |
| a | — | — | — | — | — | — | — | — | — | — |
| b | — | — | — | — | — | — | — | — | — | — |
| m | — | — | — | 5 | — | — | — | — | — | — |
| n | 0 | 0 | 0 | 0 | 0 | 0 | 0 | 0 | 0 | 0 |
| p | 0 | 0 | 0 | 0 | 0 | 0 | 0 | 0 | 0 | 0 |
| r | — | — | — | — | — | — | — | — | — | — |

| Cpd | 35 | 38 | 40 | 41 | 42 | 43 | 44 | 45 |
|---|---|---|---|---|---|---|---|---|
| A | CH | CH | CH | CH | CH | CH | CH | CH |
| B | S | S | S | S | S | S | S | S |
| R | OH | OH | OH | OH | OH | OH | OH | OH |
| R1 | H | H | H | H | H | H | H | H |
| R2 | H | H | H | H | H | H | H | H |
| R3 | H | $CH_3$ | H | H | H | H | H | H |
| R4 | H | H | H | H | H | H | H | H |
| R5 | H | H | X monomer (2) | X monomer (2) | X monomer (2) | X monomer (2) | H | H |
| R6 | OH | OH | H | H | H | H | Y monomer | Y monomer |
| R7 | — | — | — | — | — | — | — | — |
| R8 | — | — | — | — | — | — | — | — |
| R9 | — | — | — | — | — | — | — | — |
| R10 | — | — | $CH_2$ | $CH_2$ | O | O | $CH_2$ | $CH_2$ |
| R11 | OH | OH | OH | OH | OH | OH | OH | OH |
| a | — | — | 2 | 2 | 2 | 2 | 3 | 3 |
| b | — | — | 0 | 1 | 0 | 1 | 0 | 0 |
| m | — | — | — | — | — | — | — | — |
| n | 0 | 0 | 0 | 0 | 0 | 0 | 0 | 0 |
| p | 0 | 0 | 0 | 0 | 0 | 0 | 0 | 0 |
| r | — | — | — | — | — | — | 2 | 3 |

| Cpd | 46 | 47 | 48 | 50 | 51 |
|---|---|---|---|---|---|
| A | CH | CH | CH | CH | CH |
| B | S | S | S | S | S |
| R | OH | OH | N(OH)R$_8$ (4) | N(OH)R$_8$ | OH |
| R1 | H | H | H | H | H |
| R2 | H | H | H | H | H |
| R3 | H | H | H | H | H |
| R4 | H | H | H | H | H |
| R5 | H | H | H | H | H |
| R6 | Y monomer (3) | Y monomer (3) | Y monomer (4) | H | hexyl |
| R7 | — | — | — | — | — |
| R8 | — | — | $CH_3$ | Z monomer (5) | — |
| R9 | — | — | — | — | — |
| R10 | O | O | O | — | — |
| R11 | OH | OH | OH | — | OH |
| a | 3 | 3 | 3 | — | — |
| b | 0 | 0 | 0 | — | — |
| m | — | — | — | — | — |
| n | 0 | 0 | 0 | 0 | 0 |
| p | 0 | 0 | 0 | 0 | 0 |
| r | 2 | 3 | 3 | — | — |

(1) $R_8 = (CH_2)_2—O—(CH_2)_2—O(CH_2)_2$-Z where A is CH, B is S, each of $R_{1-6}$ is H, $R_{11}$ is H, n is 0 and p is 0
(2) $R_5 = (CH_2)_a(R_{10})_b(CH_2)_aR_{10}(CH_2)_a(R_{10})_b$X, where A is CH, B is S, R is OH, each of $R_{1-4}$ is H, $R_6$ is H, $R_{11}$ is OH, n is 0 and p is 0
(3) $R_6 = (CH_2)_aR_{10}(CH_2)_rR_{10}$Y, where A is CH, B is S, R is OH, each of $R_{1-5}$ is H, $R_6$ is H, n is 0 and p is 0
(4) See Formula (IV)
(5) $R_8 = (CH_2)_2—O—(CH_2)_2—O—(CH_2)_2$-Z where A is CH, B is S, each of $R_{1-6}$ is H, n is 0 and p is 0

As pointed out hereinbefore, the compounds useful in this invention include all the stereochemical modifications. The compounds of formula (I) are characterized by at least one asymmetric carbon atom marked with an asterisk (*). (Another possible chiral atom is the $R_1/R_2$ carbon). The bonds surrounding these carbon atoms are arranged tetrahedrally, and the substituents thus bonded to the asymmetric carbon atoms are in fixed positions. The compounds of formula (I) represent optical enantiomers exhibiting either the (S) or (R) configuration as shown in (i) and (ii) below, respectively:

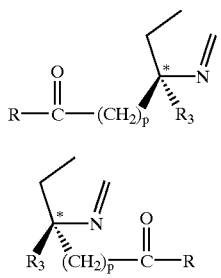

(i)

(ii)

For purpose of this application, the $R_3$ and the $(CH_2)_pC(O)R$ substituents will be designated as

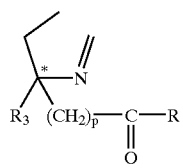

This designation is to be interpreted encompassing as the (R) and the (S) configurations, as well as racemic modifications.

Compounds useful in this invention are of either the (S) or (R) configuration, with the (S) enantiomer of formula (I) being preferred. A particular configuration can be specified according to the procedure proposed by R. S. Cahn, Sir Christopher Ingold and V. Prelog. See for example "Organic Chemistry," b $3^{rd}$ Edition, by R. T. Morrison and R N Boyd at pages 130–133. If compounds of formula (I) contain two chiral centers, e.g. when $R_1$ and $R_2$ are different, these compounds can be considered diastereomers if the stereoisomer is not a mirror image of another stereoisomer. Thus the individual enantiomers, diastereomers, racemic modifications, and mixtures are also within the scope of the invention and claims.

The invention also includes pharmaceutically-acceptable salts of the compounds of formulas (I) and (IV), particularly the carboxylic acids of formula (I). Such salts include, for example, ammonium salts and metal salts such as the alkali metal and alkaline earth metals salts, e.g., sodium, potassium, magnesium or calcium salts, as well as divalent metal salts such as zinc. Salts with suitable organic amines are also included, e.g., aliphatic, cycloaliphatic, cycloaliphatic-aliphatic or aralaphatic primary, secondary or tertiary mono-, di- or poly-amines, and also heterocyclic bases. Such amines are, for example, lower alkylamines, for example, triethylamine, hydroxy-lower alkyl-amines, for example, 2-hydroxyethylamine, bis-(2-hydroxyethyl)-amine or tris-(2-hydroxyethyl)-amine, basic aliphatic esters of carboxylic acids, for example, 4-aminobenzoic acid 2-diethylaminoethyl ester, lower alkyleneamines, for example, 1-ethylpiperidine, cycloalkylamines, for example, dicyclo-hexylamine, or benzylamines, for example, N,N'-dibenzyl-ethylenediamine, also bases of the pyridine type, for example, pyridine, colladine or quinoline. Further salts include internal salts (zwitterionic forms of compounds of the invention), wherein a basic group, for example, the basic nitrogen atom present in the pyridine ring, is protonated by a hydrogen ion originating from an acid group in the molecule.

Preparation of Compounds

The compounds useful in this invention are prepared in accordance with procedures known in the art or ascertainable therefrom or in accordance with procedure guidelines set forth in this application. For example, the following patent and laid-open applications are useful and are incorporated herein by reference: U.S. Pat. No. 4,406,905, PCT International Publication #WO 94/11367, and PCT International Publication #WO 97/36885.

Certain compounds are known and useful in the preparation of other compounds useful in this invention. These include (1) (S)-desmethyldesferrithiocin, (2) (S)-desmethyldesferrithiocin, N-methylhydroxamate In general, useful compounds where B is S, n is 0, and p is 0 are prepared by reacting a compound of formula (II) with a compound of formula (III). Formula (II) is

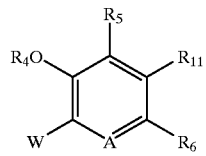

(II)

where $R_4$ is H, acyl of 1–4 carbons or alkyl of 1–4 carbons;

$R_5$ is H, OH, O-acyl of 1–4 carbons, or O-alkyl of 1–4 carbons;

$R_6$ is H, OH, alkyl of 1-6 carbons, a halogen, or is —C=C—C=C—, which, together with $R_{11}$ when $R_{11}$ is an available electron, forms a fused ring system as follows:

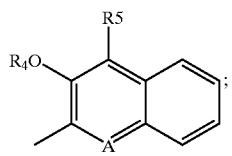

$R_{11}$ is H, OH, O-acyl of 1–4 carbons, O-alkyl of 1–4 carbons or an available electron; A is N, CH or COH; and W is carboxy or a reactive functional derivative of a carboxy group. Formula (III) is

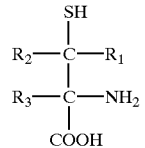

(III)

where each of $R_1$, $R_2$ and $R_3$ is H or $CH_3$. Hydroxy groups are optionally protected to produce a desired compound after splitting off optionally present protective groups and, optionally, conversion to a suitable salt or hydroxamate. An exemplary discussion of how to make compounds useful in this invention is found in U.S. Pat. No. 4,406,905, issued to Zähner, et al. on Sep. 27, 1983. This patent is incorporated herein by reference. Other discussions regarding how to make compounds useful in this invention are set forth in PCT International Publication Number WO94/11367 and WO97/36885. These too (along with any corresponding U.S. counterparts) are incorporated herein by reference.

Free hydroxy groups present in the compounds of the above formulas are optionally protected by conventional protecting groups. Such protecting groups protect the hydroxy groups from undesired condensation reactions, substitution reactions and the like. The protecting groups can be introduced and removed easily, i.e., without undesirable secondary reactions taking place, for example, by solvolysis or reduction, in a manner known per se. Protecting groups and the methods by which they are introduced and split off are described, for example, in "Protective Groups in Organic Chemistry," Plenum Press, London, New York (1973) and also in "Methoden der organischen Chemie," Houben-Weyl, 4$^{th}$ edition, Vol. 15/1, Georg Thieme Verlag, Stuttgart (1974).

Suitable hydroxy-protecting groups are, for example, acyl radicals such as lower alkanoyl optionally substituted, for example, by halogen such as 2,2-dichloroacetyl, or acyl radicals of carbonic acid semiesters, especially t-butoxycarbonyl, optionally substituted benzyloxycarbonyl, for example, 4-nitrobenzyloxycarbonyl, or 2-halo-lower alkoxycarbonyl such as 2,2,2-trichloroethoxycarbonyl, also trityl or formyl, or organic silyl radicals, also etherifying groups that can readily be split off such as t-lower alkyl, for example, t-butyl, or 2-oxa- or 2-thia-cycloalkyl having 5 or 6 ring atoms, for example, tetrahydrofuryl or 2-tetrahydropyranyl or corresponding thia analogs, and also optionally substituted 1-phenyl-lower alkyl such as optionally substituted benzyl or diphenylmethyl, there coming into consideration as substituents of the phenyl radicals, for example, halogen such as chlorine, lower alkoxy such as methoxy, and/or nitro.

A reactive functional derivative of a carboxy group W, above, is, for example, an acid anhydride, an activated ester or an activated amide, cyano, a group of the formula —C(OR$_a$)$_3$ or —C(=NH)—R$_a$ in which R$_a$ is lower alkyl. Corresponding derivatives are known in the art.

Of the anhydrides, the mixed anhydrides are especially suitable. Mixed anhydrides are, for example, those with inorganic acids such as hydrohalic acids, i.e., the corresponding acid halides, for example, chlorides or bromides, also with hydrazoic acid, i.e., the corresponding acid azides. Further mixed anhydrides are, for example, those with organic carboxylic acids such as with lower alkanecarboxylic acids optionally substituted, for example, by halogen such as fluorine or chlorine, for example, pivalic acid or trichloroacetic acid, or with semiesters, especially lower alkyl semiesters of carbonic acid such as the ethyl or isobutyl semiester of carbonic acid, or with organic, especially aliphatic or aromatic, sulfonic acids, for example, p-toluenesulfonic acid. Of the activated esters, there may be mentioned, for example, esters with vinylogous alcohols (i.e., enols such as vinylogous lower alkenols), or iminomethyl ester halides such as dimethyliminomethyl ester chloride (prepared from the carboxylic acid and, for example, dimethyl-(1-chloroethylidine)-iminium chloride of the formula (CH$_3$)$_2$N$^\oplus$=C(Cl)CH$_3$Cl$^-$, which can be obtained, for example, from N,N-dimethylacetamide and phosgene), or aryl esters such as preferably suitable substituted phenyl esters, for example, phenyl ester substituted by halogen such as chlorine, and/or by nitro, for example, 4-nitro-phenyl ester, 2,3-dinitrophenyl ester or 2,3,4,5,6-pentachlorophenyl ester, N-hetero-aromatic esters such as N-benztriazole esters, for example, 1-benztriazole ester, or N-diacylimino esters such as N-succinylamino or N-phthalylimino ester. Suitable activated amides are, for example, imidazolides, also 1,2,4-trazolides, tetrazolides or 1,2,4-oxadiazolinonides.

The activation of the carboxy group W, above, in the compounds of the above formula can also be effected in situ.

A reactive derivative of a cysteine-related compound of the above formulas is a compound in which the amino and/or mercapto group is activated for the reaction with the carboxy group of a compound of the above formulas, that is to say, is present in nucleophilic form. The amino group is activated, for example, by reaction with a phosphite.

The reaction of the above compounds in which W represents carboxy with the cysteine derivative is preferably carried out in the presence of a suitable condensation agent or under dehydrating conditions, for example, while removing the water of reaction by azeotropic distillation. Customary condensation agents are, for example, carbodiimides, for example, N,N'-diethyl-, N,N'-dipropyl-, N,N'-dicyclohexyl- or N-ethyl-N'-(3-dimethylaminopropyl)-carbodiimide, suitable carbonyl compounds, for example, carbonyldiimidazole, or 1,2-oxazolium compounds, for example, 2-ethyl-5-phenyl-1,2-oxazolium-3'-sulfomate or 2-tert.-butyl-5-methyl-isoxazolium perchlorate, for a suitable acylamino compound, for example, 2-ethoxy-1-ethoxycarbonyl-1,2-dihydroquinoline, furthermore diphenylphosphoryl azide. The condensation reaction is carried out preferably in an anhydrous reaction medium, preferably in the presence of a solvent or diluent, for example, methylene chloride, benzene or tetrahydrofuran and, if necessary, while cooling or heating, for example, at ambient temperature or at slightly elevated temperature, and/or in an insert gas atmosphere. If a compound in which W represents an acid anhydride derivative of a carboxy group is carried out, the reaction is performed under essentially the same conditions in the presence of a basic agent such as the sodium or potassium salt or carbonic acid, or a tertiary amino compound such as a tri-C$_1$–C$_4$-alkyl amine, for example, triethylamine, or a pyridine base such as pyridine or quinoline.

A preferred form of this process according to the invention is the reaction of a compound of the above formulas in which W represents cyano with a cysteine derivative of the above formula. The reaction is carried out in an inert solvent such as an aqueous solvent at ambient temperature or, preferably, at slightly elevated temperature, for example, at about 50° to 80° C., and preferably under an inert gas atmosphere. The carboxylic acid (or a reactive functional derivative thereof) is reacted with a compound of the formula

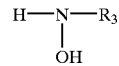

or with a compound which is convertible thereto. A preferred functional derivative of a carboxy group according to the invention is the N-succinylimino ester. The reaction is performed in an inert solvent such as an aprotic solvent, for example, dimethylformamide, dimethylsulfoxide or dioxane or a C$_1$–C$_4$ alkanol such as methanol, at ambient temperature or while cooling, for example, at about 0° C.

In resulting compounds in which one or more functional (hydroxy) groups are protected, the latter can be freed, optionally in stages or simultaneously, in a manner know per se, by means of solvolysis, especially hydrolysis or acidolysis, or in some cases also by means of carefull reduction. Silyl protecting groups are advantageously split off with fluorides, for example, tetraethylammonium fluoride.

Salts of compounds of the invention can be manufactured in a manner known per se. Thus, salts of compounds having acidic groups can be formed, for example, by treating with metal compounds such as alkali metal salts of suitable organic carboxylic acids, for example, the sodium salt of α-ethylcaproic acid, or with inorganic alkali metal or alkaline earth metal salts, for example, sodium bicarbonate, or with ammonia or a suitable organic amine, preferably stoichiometric quantities or only a small excess of the salt-forming agent being used. Acid addition salts of compounds of the invention are obtained in a customary manner, for example, by treating with an acid or a suitable anion-exchange reagent. Internal salts of compounds of the invention (zwitterionic forms) can be formed, for example, by neutralizing the compounds or salts such as acid addition salts, to the isoelectric point, for example, with weak bases, or by treating with liquid ion exchangers.

Salts can be converted in a customary manner into the free compounds: metal and ammonium salts can be converted into the free compounds, for example, by treating with suitable acids, and acid addition salts, for example, by treating with a suitable basic agent.

The starting materials are available commercially and/or known or can be manufactured by known processes.

The racemate can be split in a manner known per se, for example, after conversion of the optical antipodes into diastereoisomers, for example, by reaction with optically active acids or bases.

Where a compound is a carboxylic acid, a racemic mixture of a carboxylic acid may be resolved by first treating the racemate with an optically active amine base to form a mixture of diastereomeric salts. Examples of optically active amine bases that may be used for this purpose are (R)-(+)-∝-methylbenzylamine, (s)-(−)-∝-methylbenzylamine, (1R,2S)-(−)-ephedrine, quinine, and quinidine. The thusly formed diastereomeric salts have different properties, such as solubility, and the diastereomers may therefore be separated by selective recrystallization from a suitable solvent. The optically active carboxylic acids may then be obtained by re-acidification of the separated diastereomeric salts.

Alternatively, a racemic mixture of a carboxylic acid may be treated with an optically active alcohol to form a mixture of diastereomeric esters. Examples of optically active alcohols that may be used for this purpose are (1R,2S,5R)-(−)-menthol, (1S,2R,5S)-(+)-menthol, (R)-(−)-2-octanol, and (S)-(+)-2-octanol. The thusly-formed mixture of diastereomeric esters may then be separated by chromatography. The optically active carboxylic acids may then be obtained from the separated diastereomeric esters by conventional techniques, such as treatment of the esters with sodium hydroxide or lithium hydroxide followed by reacidification.

If a compound is an ester, a racemate of an ester may be resolved into the enantiomers by first resolving a racemic mixture of the corresponding carboxylic acid using one of the methods described above. The optically active ester may be obtained by esterification of the corresponding optically active carboxylic acid by procedures similar to those used to prepare a racemic ester.

Alternatively, a racemic mixture of a carboxylic acid or a racemic mixture of an ester may be separated into the individual enantiomers by high performance liquid chromatography using a suitable chiral stationary phase and a suitable eluent.

Further discussion of reaction parameters for compounds of this type can be found in articles by Bergeron et al. *J. Med. Chem.* 1994, 37, 1411–1417; *J. Med. Chem.* 1999, 42, 95–108; *J. Med. Chem.* 1999, 42, 2432–2440 and in patent applications U.S. Ser. Nos. 08/624,289 and 08/532,805, both of which are incorporated herein by reference.

Pharmaceutical Preparations

The compounds described above are useful for treating malaria and thus are useful for the manufacture of pharmaceutical compositions which contain an effective amount of the active substance in admixture with inorganic or organic, solid or liquid, pharmaceutically acceptable carriers. Thus, another aspect of this invention is an antimalarial composition of a compound described herein in combination with a pharmaceutically acceptable excipient.

The pharmaceutical compositions according to the invention are those which are suitable for enteral, such as oral, administration and for parenteral, such as subcutaneous or intravenous, administration to humans, and which contain the pharmacological active substance together with a pharmaceutically acceptable carrier. The dosage of the active substance depends on various factors such as the age, weight, severity of the malarial condition, and other factors a doctor might identify.

The novel pharmaceutical preparations contain from approximately 10% to approximately 95%, and preferably from approximately 20% to approximately 90%, of the active substance. Pharmaceutical compositions according to the invention can, for example, be in unit dose form, such as dragées, tablets, capsules, suppositories or ampoules, and contain from approximately 0.1 g to approximately 2.0 g, and preferably from approximately 0.3 g to approximately 1.0 g, of the active ingredient.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or draee cores. In so doing, they can also be incorporated into plastics carriers which release the active substances or allow them to diffuse in controlled amounts.

Suitable carriers are especially fillers such as sugars, for example, lactose, saccharose, mannitol or sorbitol, cellulose preparations and/or calcium phosphates, for example, tricalcium phosphate or calcium hydrogen phosphate, also binders such as starches, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators such as the above-mentioned starches, also carboxymethyl starch, cross-linked polyvinylpyrrolidone, agar, alginic acid or a salt thereof such as sodium alginate. Adjuncts are especially flow-regulating and lubricating agents, for example, silica, talc, stearic acid or salts thereof such as magnesium or calcium stearate, and/or polyethylene glycol. Dragée cores are provided with suitable coatings that are, if desired, resistant to gastric juice, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations such as acetylcellulose phthalate or hydroxypropylmethylcellulose phthalate. Coloring substances or pigments can be added to the tablets or dragée coatings, for example, for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate, for example, in admixture with fillers such as corn starch, binders and/or glidants such as talc or magnesium stearate and optionally stabilizers. In soft capsules, the active ingredient is preferably dissolved or suspended in suitable liquids or wax-like substances such as fatty oils, paraffin oil or polyethylene glycols, it being possible also for stabilizers to be added.

Other forms of oral administration are, for example, syrups prepared in a customary manner that contain the active ingredient in, for example, suspended form and in a concentration of approximately from 5% to 20%, and preferably approximately 0%, or in a similar concentration that provides a suitable single dose when administered, for example, in measures of 5 or 10 ml. Also suitable are, for example, powdered or liquid concentrates for preparing shakes, for example, in milk. Such concentrates can also be packed in single-dose quantities.

Particularly suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

Generally, an injectable composition of the invention may be 1. a solution that is ready for injection, or
2. a dry soluble composition that is ready to be combined with a solvent just prior to use,
3. or a liquid concentrate ready for dilution prior to administration. In preparing a composition for injection strict attention must be paid to tonicity adjustment to avoid irritation.

The vehicle normally has no therapeutic activity and is nontoxic, but presents the active constituent to the body tissues in a form appropriate for absorption. Absorption normally will occur most rapidly and completely when the compound is presented as an aqueous solution. However, modification of the vehicle with water-miscible liquids or substitution with water-immiscible liquids can affect the rate of absorption. Preferably, the vehicle of greatest value for subcutaneous composition is water that meets the USP specification for water for injection. Generally, water of suitable quality for compounding will either be prepared by distillation or reverse osmosis to meet these USP specifications. The appropriate specifications are spelled out in *Remington: The Science and Practice of Pharmacy*" 19<sup>th</sup> Ed. At pps. 1526–1528. In preparing the compositions which are suitable for subcutaneous injection, one can use aqueous vehicles, water-miscible vehicles, and nonaqueous vehicles Certain aqueous vehicles are recognized officially because of their valid use in parenterals generally.

Water-miscible vehicles are also useful in the formulation of the parenteral composition of this invention. These solvents are used primarily to affect the solubility of the compound. The most important solvents in this group are ethyl alcohol, polyethylene glycol and propylene glycol.

These vehicles include fixed oils, for example, those of a vegetable origin to allow for proper metabolism. For a USP subcutaneous injection injectable composition, the USP specifies limits for the degree of unsaturation and free fatty acid content. The oils most commonly used are corn oil, cottonseed oil, peanut oil, and sesame oil. Also useful are certain, more recently developed neutral oils that are esters of medium-chain fatty acids, and are also call fractionated coconut oil. Medium chain fatty acids, i.e., those of about 8 to 10 carbon atoms, include compounds referred to as MIGLYOL®, which are sold by Dynamit Nobel. Five types of MIGLYOL® identified as MIGLYOL® 810, 812, 828, 829, and 840 are useful. These are more fully described in trade literature from Dynamit Nobel. Certain other esters are also useful as nonaqueous vehicles, for example, triglycerides, propylene glycol diesters, and the like.

Additional substances may be included in the injectable compositions of this invention to improve or safeguard the quality of the composition. Thus, an added substance may affect solubility, provide for patient comfort, enhance the chemical stability, or protect preparation against the growth of microorganisms. Thus, the composition may include an appropriate solublizer, substances to make a solution isotonic, substances to act as antioxidants, and substances that act as a preservative to prevent the growth of microorganisms. These substances will be present in an amount that is appropriate for their function, but will not adversely affect the action of the composition as a treatment for malaria. Examples of appropriate antimicrobial agents include thimerasol, benzethonium chloride, benzalkoniumchloride, phenol, methyl p-hydroxybenzoate and propyl-p-hydrodxybenzoate. Appropriate buffers and antioxidants may be found in "Remingtons" at p. 1529.

Generally, the sterile, parenterally injectable composition of this invention will comprise about 0.1% by wt. to about 50% by wt. of the compound with the remainder being the appropriate excipient or excipients.

Article of Manufacture

Another aspect of this invention is an article of manufacture that comprises an antimalarial composition comprising a compound represented by formula (I) or formula (IV), in combination with a pharmaceutically acceptable excipient, the article of manufacture further comprising written instructions for administering the antimalarial composition to a human in a quantity sufficient to treat the malaria over time. This is an important aspect of the invention in that before a compound can be approved for any particular use, it must be approved for marketing by the United States Food and Drug Administration. Part of that process includes providing a label that will accompany the pharmaceutical composition which is ultimately sold. While the label will include a definition of the composition and such other items such as the clinical pharmacology, mechanism of action, drug resistance, pharmacokinetics, absorption, bioavailability, contraindications and the like, it will also provide the necessary dosage, administration and use, as discussed above. Thus, the combination of the drug with appropriate labeling instructions is important for the proper usage of the drug once it gets on the market.

Treatment of Malaria

The term "treatment" as used herein covers any treatment of a disease treatable by an iron chelator in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

Malaria is a disease that strikes various mammals, particularly humans and non-human primates, as well as certain birds. The compounds and compositions of this invention may be used to treat malaria in mammals and birds. Its primary application will be in treating humans in which a malignant form of malaria is caused by the protozoan known as *Plasmodium falciparum*, although the compounds may be used also to treat malaria caused by more benign protozoans, such as *P. vivax, P. malariae*, and *P. ovale*. The compounds are delivered at a level and for a time that deprives the parasite of iron for its metabolic processes, thus causing death of the parasites.

In general, the compounds of the invention may be administered enterally, that is orally, or parenterally (i.e. intraperitoneally—IP; intramuscularly—IM; subcutaneously—SC; intravenously—IV; etc.), such as by single injection or infusion by IV. By subcutaneous administration it is meant that the drug in the form of an appropriate injectable composition is injected into the areola connective tissue just below the skin. The injection may be a solution, a suspension, or a formulation that provides a controlled release of the active entity. Generally, the subcutaneous administration will be done with excipients that are suitable for subcutaneous administration, which means that the excipients will have to meet USP considerations in being appropriate for injectable compositions. Thus, the composition will need to be sterile to avoid any complications due to insterility at the injection site. The particular mode of treatment will depend on the severity of the disease, the age of the patient, the size of the patient, the relative health of the patient, and other factors of which the treating physician will be aware. The amount of the active ingredient that will be present in the composition to be injected and that will be injected is a therapeutically-effective amount, that is, an amount which is sufficient to result in successful treatment as defined above when administered to an animal exhibiting signs and symptoms of malaria. The therapeutically effective amount will vary depending on the subject, the severity of the affliction and the manner of administration, and may be determined routinely by one of ordinary skill in the art in light of the disclosure of this specification. For example, if a patient is extremely ill and is unable to ingest any food, then it may be necessary to provide a single injection or an IV infusion over a period that may be up to 72 hours. While in some cases, treatment could last up to a month, usually the treatment regimen will last no more than two weeks, preferably less than one week. The patient will be monitored by indications that the signs and symptoms are improving.

Suitable doses are in the general range from about 1 to about 250 mg/Kg body weight of the recipient per day, preferably in the range from about 5 to about 150 mg/Kg.

The following examples are given to teach one of ordinary skill in the art how to make compounds usefull in this invention. The numerical reference to a compound refers to the compounds set forth in Table I of this application. The designation of formula A, B, C, etc. refers to the reaction sequence or scheme accompanying the example. DFT refers to desferrithiocin.

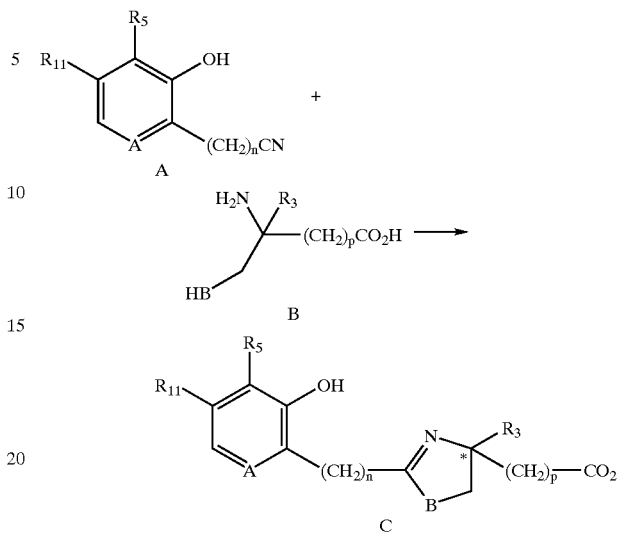

Scheme 1

EXAMPLE 1

Synthesis of Compounds 2,3 5–7,9, 14–17 and 22–24

Compounds 2, 3, 5–7, 9 and 14–17 with the general formula C, were synthesized by cyclocondensation of an o-hydroxyaryl nitrile A with a cysteine derivative B (Scheme 1) (Bergeron et al., *J. Med. Chem.* 34: 2072–2078 (1991); Bergeron et al., *J. Med. Chem.* 37:

1411–1417 (1994); Bergeron et al., *J. Med. Chem.* 42: 2432–2440 (1999);

(S)- and (R)-DesmethylDFTs 2 were synthesized by condensation of 2-cyano-3-hydroxypyridine, obtained from 3-hydroxypyridine-N-oxide, with D- or L-cysteine, respectively, in pH6 phosphate buffer and methanol. Reaction of 2-hydroxypyridine with D- or L-cysteine provided (S)- and (R)-desazadesmethylDFTs 3, respectively.

The production of (S)-desazaDFT (9), identical to the natural product 4-methylaeruginoic acid (Ryoo et al., *J. Antibiot.* 50: 256–258 (1997)), and 4'-hydroxydesazaDFT (28) was accomplished by cyclocondensation of 2-cyanophenol or 2,4-dihydroxybenzonitrile, respectively, with (S)-α-methyl cysteine in buffered aqueous $CH_3OH$. The latter cyano compound was prepared by treatment of 2,4-dihydroxybenzaldehyde with nitroethane in sodium acetate and acetic acid. Hydrolysis of DFT (1) in 6 N HCl generated the unusual amino acid (S)-α-methyl cysteine.

Tridentate chelators 15–17, homologues of (S)-3 with a spacer between the ligating centers, were synthesized as follows. (S)-4,5-Dihydro-2-(2-hydroxyphenylmethyl)-4-thiazolecarboxylic acid (15) was assembled by heating D-cysteine with 2-hydroxyphenylacetonitrile in methanolic phosphate buffer. (S)-4,5-Dihydro-2-(2-hydroxyphenyl)-4-thiazoleacetic acid (16) and (S)-4,5-dihydro-2-(2-hydroxyphenyl)-4-thiazolepropanoic acid (17) were made by reacting (S)-3-amino-4-mercaptobutanoic acid or (S)-4-amino-5-mercaptopentanoic acid, respectively, and 2-cyanophenol in methanolic phosphate buffer. The β- or γ-amino acid was in turn prepared from partially protected L-aspartic and L-glutamic acid (Chauvel et al., *J. Med. Chem.* 37: 1339–1346 (1994); Wilk et al., *Neuropeptides* 16: 163–168 (1990)).

(R)- and (S)-4,5-Dihydro-2-(2-,4-dihydroxyphenyl)-4-thiazolecarboxylic acid (5) were constructed by condensing 2,4-dihydroxybenzonitrile with L- or D-cysteine, respectively, in phosphate buffer and methanol.

The key step of the synthesis of (S)-4,5-dihydro-2-(2-hydroxy-3-methoxyphenyl)-4-thiazolecarboxylic acid (6) was cyclocondensation of D-cysteine with 2-hydroxy-3-methoxybenzonitrile. The cyano intermediate was obtained from o-vanillin by treatment with nitroethane in sodium acetate and acetic acid. (S)-4,5-Dihydro-2-(2-hydroxy-4-carboxyphenyl)-4-thiazolecarboxylic acid (7) was synthesized by a similar reaction sequence. 4-Formyl-3-hydroxybenzoic acid was converted to 4-cyano-3-hydroxybenzoic acid using nitroethane in sodium acetate and acetic acid; cyclization with D-cysteine completed the synthesis of dicarboxylic acid chelator 7.

Condensation of 2-cyano-3-4-hydroxypyridine with DL-homocysteine afforded racemic 2-(3-hydroxy-2-pyridinyl)-4H-5,6-dihydro-1,3-thiazine-4-carboxylic acid (14), a six-membered analogue of 2 (Scheme 1) (Bergeron et al., *J. Med. Chem.* 37: 1411–1417 (1994)).

EXAMPLE 2
Synthesis of Compounds 18–20

Fused ring DFT analogue J, specifically compounds 18–21, were synthesized by cyclization of an enantiomer of cysteine B ($R_3$=H, B=S, p=0) with an o-hydroxynaphthyl or -quinolinyl nitrile I (Scheme 2) (Bergeron et al., *J. Med. Chem.* 39: 1575–1581 (1996)).

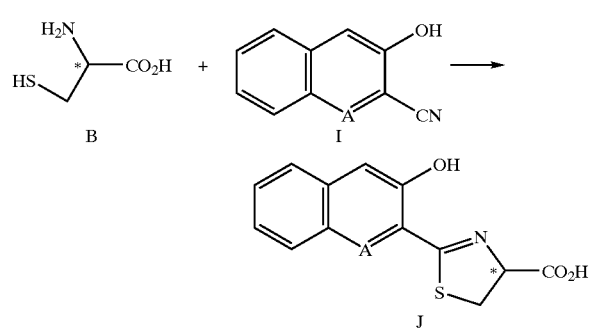

EXAMPLE 3
Synthesis of Compounds 22–24

Conversion of the carboxylic acid group of (S)-desmethyldesferrithiocin (DMDFT, 2), to an N-methylhydroxarnate or to the pentacoordinate dihydroxamate compound resulted in compounds 22 and 23, respectively (Bergeron, et al., *J. Med. Chem.* 37: 1411–1417 (1994)).

Compound 24, the N-benzylhydroxamate of 2, was synthesized by N-acylation of N-benzylhydroxylamine hydrochloride with 2 activated by (benzotriazol-1-yloxy)tris(dimethylamino)phosphonium hexafluorophosphate (BOP reagent) in N,N-diiso-propylethylamine (DIEA; 3 equiv) and DMF (Scheme 8). Although it was possible to isolate an optically active hydroxamate via Sephadex LH-20 chromatography, the compound epimerized on recrystallization. The magnitude of optical rotation decreased from $[\alpha]_D$=−16.4° to essentially zero. Because of the spontaneous epimerization, no attempt was made to evaluate the biological properties of optically active materials. The racemic product was utilized in all of the studies.

EXAMPLE 4
Synthesis of Compounds 29, 29a, 33, 35 and 38

Compound 29 was synthesized by condensation of 2,5-dihydroxybenzonitrile

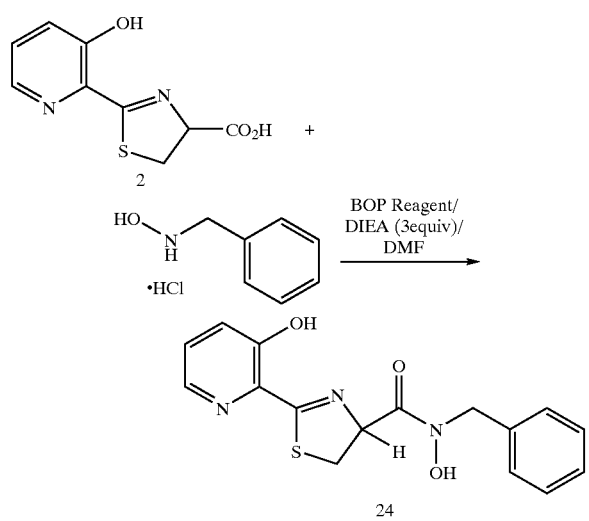

with D-cysteine as described in Scheme 1. This aryl nitrile, in turn, was made by heating 2,5-dihydroxybenzaldehyde with nitroethane in sodium and acetic acid.

By analogy to the synthesis of 5'-hydroxydesazadesmethylDFT 29, (S)-4,5-dihydro-2-(2,5-dihydroxyphenyl)-4-methyl-4-thiazolecarboxylic acid (5'-hydroxydesazaDFT, 33) is generated from the cyclocondensation of (S)-α-methyl cysteine with 2,5-dihydroxybenzonitrile in buffered aqueous CH3OH. Isomeric dihydroxy desazadesmethylDFT 35 is synthesized from the requisite aryl nitrites and D-cysteine in methanolic phosphate buffer (pH 6). Dihydroxy desazaDFT 38 is prepared by treatment of (S)-α-methyl cysteine with the same set of trihydroxybenzonitriles. Heating 2,4,5-trihydroxybenzaldehyde with nitroethane in sodium acetate and acetic acid provides the corresponding trihydroxybenzonitrile, aromatic precursors to compounds 35 and 38.

(S)-4,5-Dihydro-2-(5-fluoro-2-hydroxyphenyl)-4-thiazolecarboxylic acid (5'-fluorodesazadesmethylDFT, 29a) is prepared from the cyclization of D-cysteine onto 5-fluoro-2-hydroxybenzonitrile in slightly acidic buffer. The aromatic precursor could be made by direct cyanation of p-fluorophenol using methyl thiocyanate, aluminum chloride, and boron trichloride in ethylene dichloride followed by heating in aqueous base (Adachi et al., *Syn. Commun.* 20:71–84 (1990)).

EXAMPLE 5

Synthesis of Compounds 40–43

The synthesis of bis-DFT compounds 40 and 41 is dependent on the relative acidity of the C-2 proton of 1,3-dimethoxybenzene (51), which has been metalated (n-BuLi/THF) then alkylated in the 2-position with 1-bromopropane (Brown et al., *J. Med. Chem.* 32: 807–826 (1989) and 1,4-diiodobutane (Tanaka et al., *Chem. Lett.*: 1905–1908 (1989)) in the latter case joining two aromatic rings. Thus, deprotonation and regiospecific aklylation of 51 with 1,9-dichlorononane (52a) or 1,11-dibromoundecane (52b), respectively, affords tetramethoxy compounds 53a,b (Scheme 3). The four methyl protecting groups are removed with $BBr_3/CH_2Cl_2$, yielding tetraphenols 54a,b. Vilsmeier-Haack formylation ortho to a phenol of each ring ($POCl_3/DMF/CH_3CN$) gives dialdehydes 55a,b which are directly converted to dinitriles 56a,b with nitroethane/NaOAc in HOAc (Karmarkar et al., *Synthesis*: 510–512 (1985). We have recently formylated 2-methylresorcinol under these conditions to yield 2,4-dihydroxy-3-methylbenzaldehyde, which was carried through to (S)-4,5-dihydro-2-(2,4-dihydroxy-3-methylphenyl)-4-thiazolecarboxylic acid. To complete the synthesis of hexadentate chelators 40 and 41, bis nitriles 56a,b are reacted by D-cysteine (>2 equiv) in pH 6 buffer.

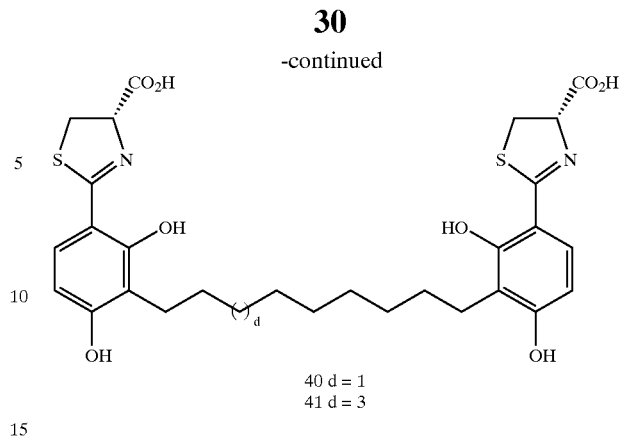

40 d = 1
41 d = 3

The analogous ether-containing ligands 42 and 43 are synthesized starting with 1,3-bix(benzyloxy)benzene (57) (Haraldsson et al., *Tetrahedron* 53: 215–224 (1997)), which is methylated then alkylated in the 2-position with 0.5 equivalent of 4-chlorobutyl ether (58a) or tetra(ethylene glycol) di-p-tosylate (58b), respectively (Scheme 4). The phenols are protected by benzyl groups instead of methyls since treatment with $BBr_3$ would cleave the ether-containing tethers along with the methyl ethers. The resulting symmetrical compounds 59a,b are catalytically deprotected under mild conditions (1 atm, Pd/C, $CH_3OH$), affording tetraphenols 60a,b. Completion of the synthesis of 42 and 43 is carried out as in Scheme 3.

Scheme 3

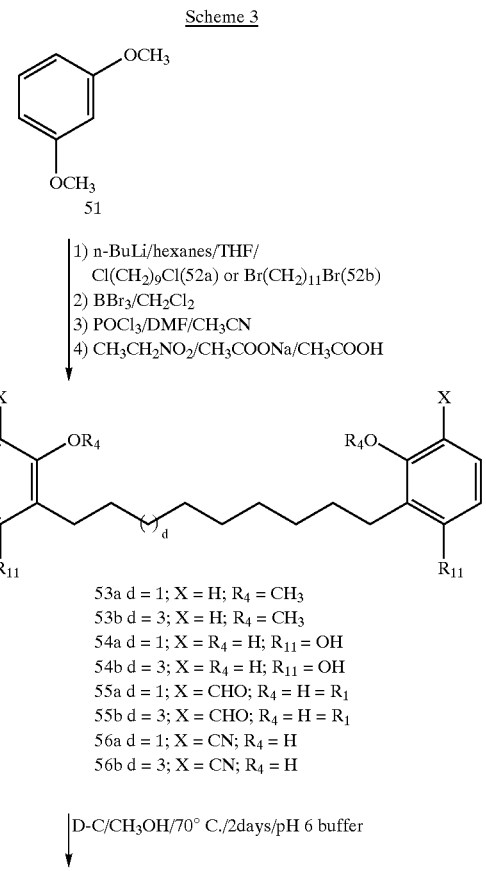

Scheme 4

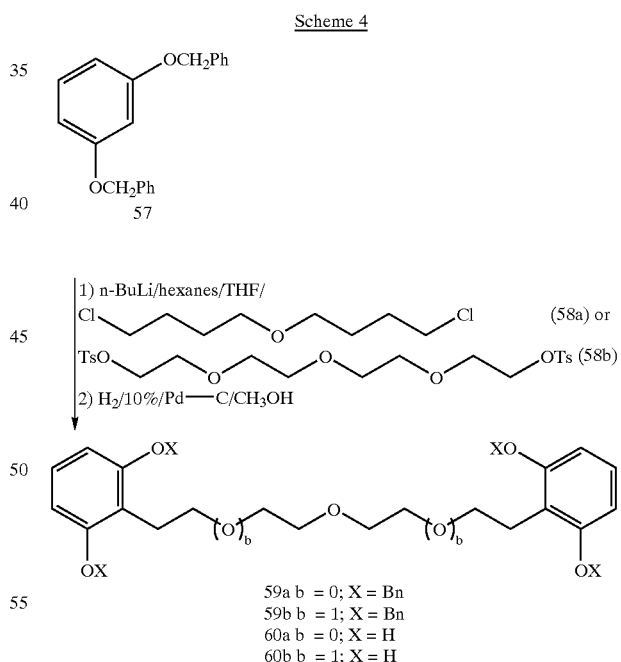

59a b = 0; X = Bn
59b b = 1; X = Bn
60a b = 0; X = H
60b b = 1; X = H

EXAMPLE 6

Synthesis of Compounds 44–50

The preparation of bis DFT compounds 44 and 45 depends on the ability to acylate resorcinol (61) at C-4 (Scheme 5). Specifically, heating sebacic acid (62a) or undecanedioic acid (62b) with 61 in trifluoromethanesulfonic acid (Koch et al., *J. Org. Chem.* 59: 1216–1218

(1994)) gives diketones 63a,b. The carbonyl groups are then changed into methylenes with hydrogen (Pd-C/AcOH) (Horning et al., *J. Am. Chem. Soc.* 71: 1036–1037 (1949)) providing tetraphenols 64a,b. The Vilsmeier-Haack reaction leads to dialdehydes 65a,b such that the connector is in the 5-position of the rings. After conversion to the dinitriles 66a,b as above, cyclocondensation with D-cysteine (>2 equiv) under weakly acidic conditions generates 44 and 45, respectively.

The oxa substituted tethers for chelators 46 and 47 are made in a stepwise manner (Scheme 6). 3-(2,4-Dihydroxyphenyl)propionic acid (67) is transformed into the tribenzyl derivative 68; reduction of the ester with LiAlH$_4$ in THF provides carbinol 69, in which the phenols remain benzyl protected (Amsberry et al., *J. Org. Chem.* 55: 5867–5877 (1990)). Two equivalents of primary alcohol 69 are linked by treatment of its alkoxide with ethylene diiodide (70a) or 1,3-diiodopropane (70b). Adducts 71a,b are then catalytically debenzylated to afford diethers 72a,b. Completion of the synthesis of compounds 46 and 47 is accomplished using the methodology of Scheme 5.

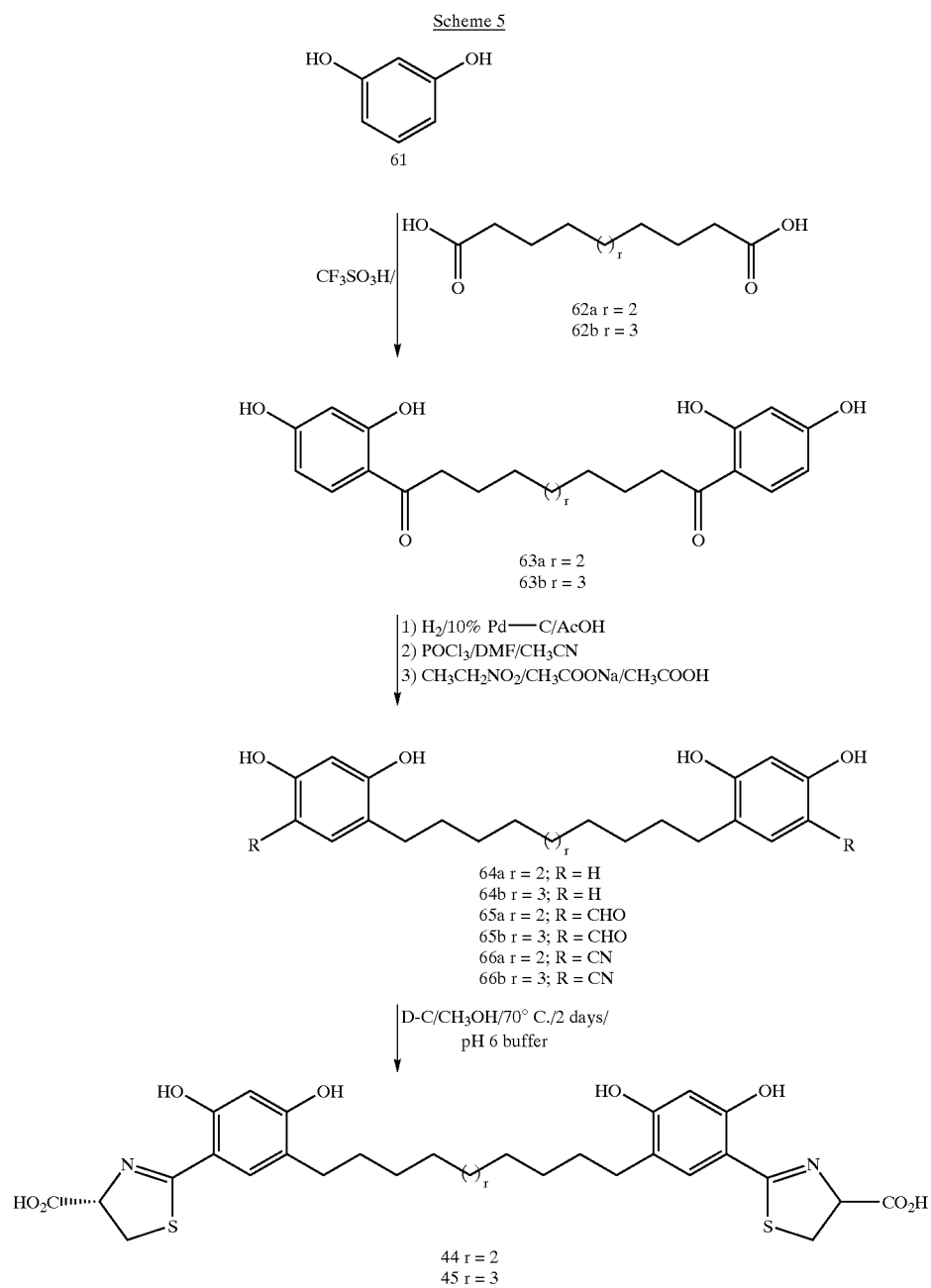

Scheme 6

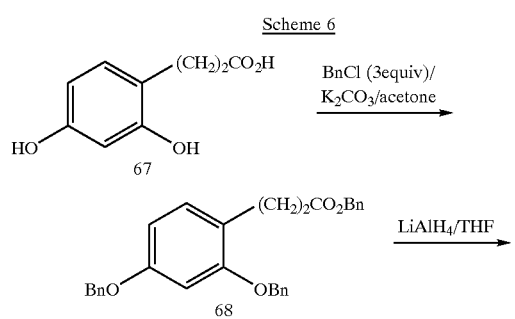

Coupling of diacid 47 with N-methylhydroxylamine (2 equiv) using BOP reagent (excess DIEA, DMF) (Bergeron et al., *J. Med. Chem.* 37: 1411–1417 (1994)) provides bis-hydroxamate 48. N-Acylating dihydroxylamine 73 with the same dicarboxylic acid (1:1) and coupling reagents under high dilution conditions leads to macrocyclic chelator 49. Analogous reaction of the dihydroxylamine K' (Bergeron et al., *J. Med. Chem.* 42: 2881–2886 (1999)) with 2 equivalents of 4'-hydroxydesazadesmethylDFT (25) (Bergeron et al., *J. Med. Chem.* 42; 95–108 (1999)) generates hexadentate chelator 50 (Scheme 7).

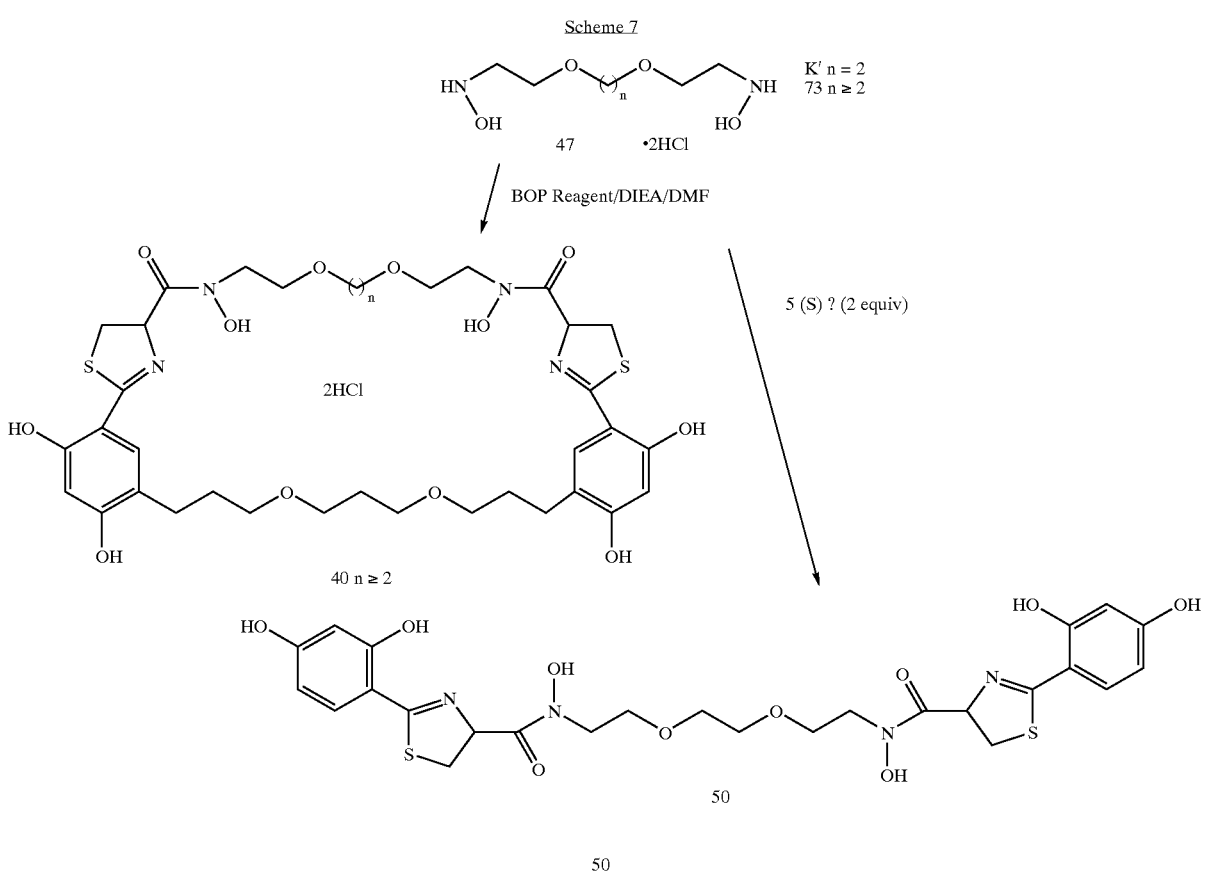

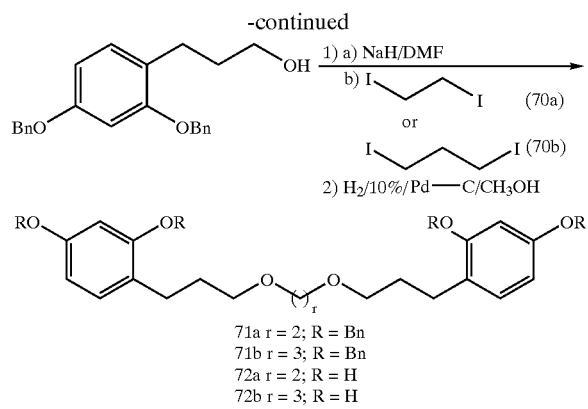

EXAMPLE 7

Synthesis of Compound 25

Compound 25 was generated by N-acylation of N-aklyhydroxylamines (K) with (S)-desmethylDFT (2) (Scheme 9) (Bergeron et al., *J. Med. Chem.* 37:1411–1417 (1994); Bergeron et al., *J. Med. Chem.* 42:2881–2886 (1999)). Hexacoordinate compound 25, (S,S)-$N^1$,$N^8$-bis[4,5-dihydro-2-(3-hydroxy-2-pyridinyl)-4-thiazoyl]-$N^1$,$N^8$-dihydroxy-3,6-dioxa-1,8-octanediamine, resulted from N-acylation of $N^1$,$N^8$-dihydroxy-3,6-dioxa-1,8-octanediamine at each terminus with acid 2 using BOP.

Scheme 9

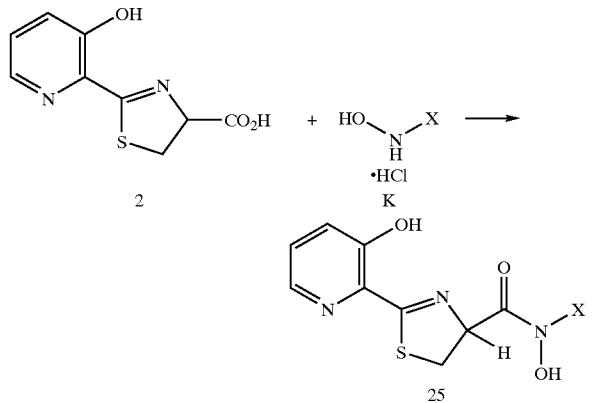

EXAMPLE 8
Compounds Useful in the Invention

A. Preparation of a compound of formula (I) where A is CH; each of $R_1$, $R_2$, $R_3$, $R_4$, $R_5$, $R_6$ and $R_{11}$ is H; nis 0; p is 0; and C(O)R is COOH.

2,4-Dihydroxybenzonitrile was prepared according to the method of Marcus in *Ber. Dtsch. Chem. Ges.* 1981, 24, 3651, as follows:

A mixture of 2,4-dihydroxybenzaldehyde (5.0 g, 36.2 mmol), sodium acetate (5.94 g, 72.4 mmol), nitroethane (5.44 g, 72.4 mmol) and glacial acetic acid (10 ml) was refluxed for 6 hours. After cooling, the mixture was poured onto ice (100 g) and extracted with ethyl acetate (4×50 ml). The combined organic layers were washed with saturated $NaHCO_3$ until the pH of the aqueous layer remained at 8, dried ($Na_2SO_4$), and the solvent removed in vacuo. Flash chromatography ($SiO_2$, cyclohexane: ethyl acetate—1:1) afforded 2,4dihydroxybenzonitrile (2.87 g, 59%) as a pale yellow solid. $^1$H NMR (300 MHz, DMSO-$d_6$) δ6.33 (d, 1H, J=8.6 Hz), 6.43 (s, 1H), 7.37 (d, 1H, J=8.6 Hz), 10.35 (s, 1 H), 10.78 (s, 1H). IR (KBr) 2200 $cm^{-1}$.

D-cysteine hydrochloride monohydrate (6.8 g, 38.7 mmol) was added to a solution of 2,4-dihydroxybenzonitrile (3.5 g, 25.9 mmol), prepared as described above, in a mixture of degassed methanol (105 ml) and 0.1 M phosphate buffer, pH 5.95 (70 ml). $NaHCO_3$ (3.25 g, 38.7 mmol) was carefully added and the mixture was stirred at 70° C. under Argon for 54 hours. Volatile components were removed under reduced pressure and the solution was acidified with 1 N HCl to pH 2. The resulting brown precipitate was vacuum filtered and the solid was washed with water (40 ml) and ethanol (20 ml). The crude product was dissolved in saturated $NaHCO_3$ (700 ml) and the aqueous solution washed with ethyl acetate (2×200 ml). The aqueous layer was filtered through a fine frit and acidified with 1 N HCl to pH 2. The precipitated product was vacuum filtered. The aqueous layer was extracted with ethyl acetate (4×400 ml), the combined organic extracts were dried ($Na_2SO_4$) and the solvent was removed in vacuo. The remaining solid was combined with the precipitated product and dried under high vacuum at 40° C. for 12 hours to give 4,5-dihydro-2-(2,4-dihydroxyphenyl)-thiazole-4(S)-carboxylic acid (4.08 g, 66%), mp 266–268° C. (dec) (*Ind. J. Chem., Vol.* 15B, Kishore et al, pages 255–257 (1977) for (L)-isomer: 261–262° C.). $^1$H NMR (300 MHz, DMSO-$d_6$) δ3.61 (m, 2 H), 5.38 (dd, 1H, J=7.2/9.4 Hz), 6.31 (d, 1H, J=2.3 Hz), 6.38 (dd, 1H, J=2.3/8.6 Hz), 7.25 (d, 1H, J=8.6 Hz), 10.25 (br s, 1H), 12.60 (br s, 1H), 13.15 (br s, 1 H). Anal. Calc. For $C_{10}H_9NO_4S$: C, 50.20, H 3.79, N 5.85. Found: C, 50.13, H 3.82, N 5.85.

B. Preparation of a compound of formula (I) where A is N; each of $R_1$, $R_2$, $R_3$, $R_4$, $R_5$, $R_6$ and $R_{11}$ is H; n is 0, p is 0 and C(O)R is COOH.

By following the procedure of Part A of this example, but substituting the corresponding pyridyl aldehyde for 2,4-dihydroxybenzaldehyde, the corresponding pyridyl compound: 4,5-dihydro-2-(3',5'-dihydroxypyrid-2'-yl)-thiazole-4(S)-carboxylic acid.

EXAMPLE 9
Compound Useful in this Invention

A. Preparation of a compound (S)-desmethyldesferrithiocin, N-methylhydroxamate.

Benzotriazol-1-yloxytris(dimethylamino)phosphonium hexafluorophosphate (BOP) (442.3 mg, 1.0 mmol) was added to a solution of (S)-desmethyldesferithiocin [See Example 1] (224.2 mg, 1.0 mmol) and N-methylhydroxylamine hydrochloride (83.52 mg, 1.0 mmol) in dimethylformamide (DMF) (8 ml) at 0° C. A solution of diisopropylethylamine (DIEA, 129.2 mg, 1.0 mmol) in DMF (2 ml) was added dropwise to the above solution at 0° C. The mixture was stirred at 0° C. for 15 minutes and at room temperature overnight. Solvent was removed under high vacuum and the residue was treated with ethyl acetate (EtOAc, 30 ml). The organic phase was washed with 10 ml portions of saturated $NaHCO_3$, saturated NaCl, 10% citric acid and saturated NaCl, and solvent was removed by rotary evaporation. Purification of the residue on a Sephadex LH-20 column, eluting with 3% EtOH/toluene, produced 120 mg of (S)-desmethyldesferrithiocin, N-methylhydroxamate (47%) as a yellow solid: α 25–41.3° (c 2.34); NMR (CDCl$_3$/d$_6$DMSO) δ3.27 (s, 3H) 3.53 (dd, 2H, J=9, 6), 5.70 (t, 1H, J=9), 7.30 (d, 2H, J=3), 8.10 (t, 1H, J=3). Anal. calculated for ($C_{10}H_{11}N_2O_3S$): C, 47.42; H, 4.38; N, 16.59. found: C, 47.66; H, 4.41; N, 16.45.

EXAMPLE 10
Animal Models

One screen for efficacy is the normal (not iron-loaded) Sprague-Dawley rat with a cannulated bile duct. In this model, collection of bile and urine after oral or parenteral administration of a chelator permits the rapid determination of the magnitude and route(s) of excretion. The iron-loaded *Cebus apella* monkey is used as a better screen, however. To date, the behavior of iron chelators in this primate model has been quantitatively predictive of both the magnitude and routes of iron clearance after human administration.

The primary measure of activity is the efficiency of the compound, as assessed in both rodent and primate models and compared with sc DFO. Compound efficiency is a comparative evaluation of how much iron excretion a chelator promotes relative to the theoretical amount. For example, the hexacoordinate chelator DFO forms 1:1 iron complexes with a formation constant of $3 \times 10^{30}$ $M^{-1}$ (Anderegg et al., *Helv. Chim. Acta* 46: 1409–1422 (1963)); if the efficiency were 100%, one mmol of DFO administered to an animal would cause one mmol of the iron complex to be excreted. In fact, only 5% of the calculated iron is excreted when DFO is administered to humans (Kirking et al., *Clin. Pharmacol.* 10:775–783 (1991)). In the case of the DFT analogues, the efficiency calculation is based on the formation of a 2:1 complex with a formation constant assumed to be similar to that of the parent compound, $4 \times 10^{29}$ $M^{-1}$ (Anderegg et al., *J. Chem. Soc., Chem. Commun.* 1194–1196 (1990)).

The results are shown below in Table II.

TABLE II

% Efficiency of Iron Clearance

| Compound | Rat | Monkey |
|---|---|---|
| 1(S) | 5.5 ± 3.2 | 16.1 ± 8.5 (150 µmol/kg po) |
| 2(S) | 2.4 ± 0.56 (po) | 4.8 ± 2.7 (150 µmol/kg po) |
|  | 1.8 ± 0.7 (sc) | 8.0 ± 2.5 (300 µmol/kg po) |
|  |  | 8.3 ± 2.7 (300 µmol/kg sc) |
| 2(R) | 3.9 ± 1.8 | 0.5 ± 2 (300 µmol/kg po) |
| 3(S) | 1.4 ± 0.6 (po) | 12.4 ± 7.6 (300 µmol/kg po) |
| 3(R) | 4.2 ± 1.6 (po) | 8.2 ± 3.2 (300 µmol/kg po) |
| 15(S) | ≦0.5 |  |
| 16(S) | ≦0.5 |  |
| 17(S) | ≦0.5 |  |
| 9(S) | 2.7 ± 0.5 (po) | 21.5 ± 12 (75 µmol/kg po) |
|  |  | 13.1 ± 4 (300 µmol/kg po) |
|  |  | 43.3 ± 8.5 (300 µmol/kg sc) |
| 14(S) | ≦0.5 |  |
| 5(S) | 2.4 ± 0.9 (po) | 4.2 ± 1.4 (150 µmol/kg po) |
|  |  | 5.6 ± 0.9 (150 µmol/kg in $H_2O$ sc) |
| 5(S) |  | 5.3 ± 1.7 (300 µmol/kg po) |
|  |  | 4.8 ± 1.4 (300 µmol/kg in $H_2O$ po) |
| 5(R) | ≦0.5 | 1.7 ± 0.8 (150 µmol/kg po) |
| 18 | 2.9 ± 1.3 | 0.7 ± 0.3 (300 µmol/kg po) |
| 19 | 3.7 ± 1.1 | 2.1 ± 0.7 (300 µmol/kg po) |
| 20 | 12.3 ± 3.2 | ≦0.5 (75 µmol/kg po) |
| 21 | 5.9 ± 3.2 | 3.5 ± 1.8 (150 µmol/kg po) |
| 6(S) | 0.9 ± 0.3 (po) |  |
|  | 0.5 ± 0.9 (sc) |  |
| 7(S) | ≦0.5 |  |
| 28(S) | ≦0.5 | 17.7 ± 3.9 (75 µmol/kg po) |
|  |  | 13.4 ± 5.8 (150 µmol/kg po) |
| 32 | 4.6 ± 2.1 (po) |  |
|  | 20.6 ± 1.3 (sc) |  |
| 22 | 3.1 ± 0.4 (po) | 6.9 ± 3.0 (150 µmol/kg po) |
|  | 5.3 ± 0.7 (sc) | 13.2 ± 7.7 (300 µmol/kg po) |
|  |  | 11.7 ± 5.5 (150 µmol/kg sc) |
| 23 | 2.8 ± 0.8 (po) | 3.2 ± 2.0 (225 µmol/kg po) |
|  | 8.5 ± 0.4 (sc) | 12.8 ± 3.4 (225 µmol/kg sc) |
| 24 | 1 ± 0.1 (po) | ≦0.5 (300 µmol/kg po) |
|  | 1.4 ± 0.8 (sc) | ≦0.5 (300 µmol/kg sc) |
| 25 | 4.6 ± 2.1 (po) |  |
|  | 20.6 ± 1.3 (sc) |  | po (oral) and sc (subcutaneous) refer to the route of administration

EXAMPLE 11

Impact of Desferrithiocin Analogs on Malarial Parasites In Vitro

Studies can be done on the developmental stages and morphology of the malarial parasite in vitro; the minimum effective concentration required for cytotoxicity can be shown. The target structures include the nuclear envelope, the membrane of the food vacuole, accumulation of electron-dense substances in the mitochondria, undigested materials, and dilation of the endoplasmic reticulum.

In order to determine the concentration at which a compound is cytostatic and cytotoxic, the parasites are exposed to the drug using at least two different concentrations. After 48 h the chelator is removed, and the parasites are incubated for an additional 48 h. The percent parasitemia is determined at both time points (48 and 96 h). The effects of the various compounds on malarial parasites seem quite varied. For the purposes of comparison, DFO can serve as the positive control. DFO inhibits malarial growth during an initial 48-h continuous exposure at $10^{-5}$ M, normal growth resumes after the compound is removed. However, at a concentration of $10^{-4}$ M, DFO is cytotoxic; the plasmodia die during the 48-h incubation with the compound.

The compounds designated as 8 and 22 in Table I are active in this in vitro assay. Others can be similarly tested.

What is claimed is:

1. A pharmaceutical composition comprising a compound represented by formula (I) or (V), in combination with a pharmaceutically acceptable excipient, wherein formulas (I) and (V) are

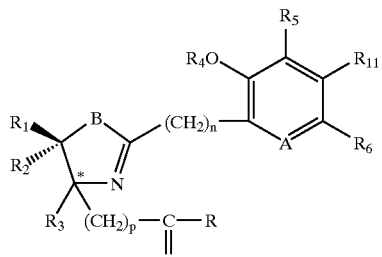
(I)

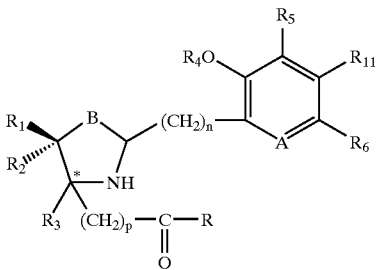
(V)

where:
R is OH, $OR_7$, or $N(OH)R_8$;
$R_1$ is H, $CH_3$ or absent;
$R_2$ is H, $CH_3$ or absent, provided that $R_1$ and $R_2$ are not both absent;
$R_3$ is H or $CH_3$, or $R_3$ is absent when one of $R_1$ or $R_2$ is absent forming a double bond between the $R_1/R_2$ carbon and the $R_3$ carbon;
$R_4$ is H, acyl of 1–4 carbons or alkyl of 1–4 carbons;
$R_5$ is $((CH_2)_a(R_{10}))_b(CH_2)_aR_{10}((CH_2)_a(R_{10}))_bX$;
$R_6$ is H, OH, alkyl of 1–6 carbons or a halogen, or $R_6$ is —C=C—C=C—, which, together with $R_{11}$ forms a fused ring system as follows:

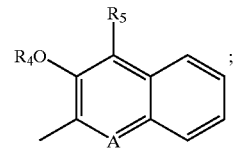

$R_7$ is alkyl of one to four carbons or optionally substituted benzyl;
$R_8$ is H, alkyl of one to four carbons, optionally substituted benzyl, or

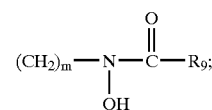

$R_9$ is H, alkyl of one to four carbons or optionally substituted benzyl;
$R_{10}$ is O or $CH_2$;
$R_{11}$ is H, OH, O-acyl of 1–4 carbons or O-alkyl of 1–4 carbons or $R_{11}$ is part of a fused ring system when $R_6$ is —C=C—C=C—;

A is CH or C(OH);
B is S, O, N or $CH_2$;
a is 2 or 3;
b is 0 or 1;
m is an integer from 1 to 8;
n is 0 or 1;
p is 0, 1 or 2; and
X is X is

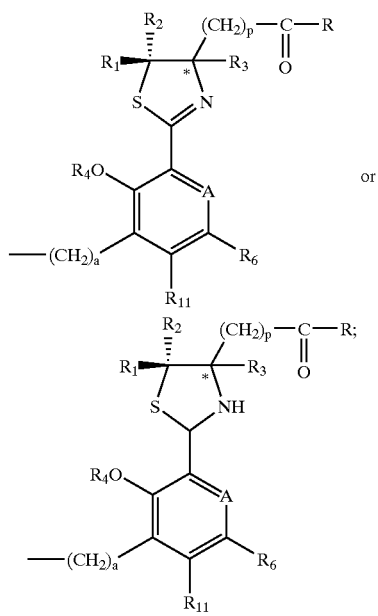

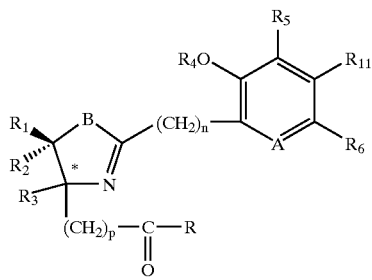

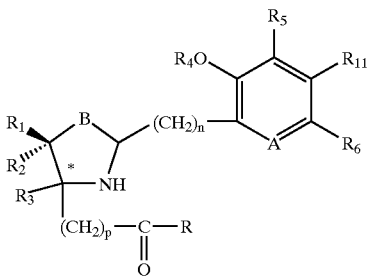

wherein each of the substituents shown is defined above,
or a pharmaceutically acceptable salt of the compound represented by formula (I) or (V)
or a stereoisomer of the compound or mixture of stereoisomers.

2. The composition of claim 1, wherein A is CH.
3. The composition of claim 2, wherein B is S, and n and p each is 0.
4. The composition of claim 3, wherein $R_4$ is H.
5. The composition of claim 4, wherein R is OH.
6. The composition of claim 5, wherein $R_{11}$ is H.
7. The composition of claim 5, wherein $R_{11}$ is OH.
8. The composition of claim 5, wherein $R_{11}$ is OH, and each of $R_1$ and $R_2$ is H.
9. The composition of claim 8, wherein a is 2 and each of $R_3$ and $R_6$ is H.
10. The composition of claim 9, wherein $R_{10}$ is $CH_2$ and b is 0.
11. The composition of claim 9, wherein $R_{10}$ is $CH_2$ and b is 1.
12. The composition of claim 9, wherein $R_{10}$ is O and b is 0.
13. The composition of claim 9, wherein $R_{10}$ is O and b is 1.
14. A pharmaceutical composition comprising a compound represented by formula (I) or (V), in combination with a pharmaceutically acceptable excipient, wherein formulas (I) and (V) are where:

R is $N(OH)R_8$;

$R_1$ is H, $CH_3$ or absent;

$R_2$ is H, $CH_3$ or absent, provided that $R_1$ and $R_2$ are not both absent;

$R_3$ is H or $CH_3$, $R_3$ is absent when one of $R_1$ or $R_2$ is absent forming a double bond between the $R_1/R_2$ carbon and the $R_3$ carbon;

$R_4$ is H, acyl of 1–4 carbons or alkyl of 1–4 carbons;

$R_5$ is H, OH, O-acyl of 1–4 carbons or O-alkyl of 1–4 carbons;

$R_6$ is H, OH, alkyl of 1–6 carbons or a halogen, or $R_6$ is —C=C—C=C—, which, together with $R_{11}$ forms a fused ring system as follows:

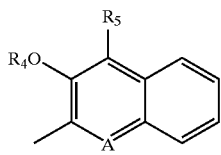

$R_8$ is

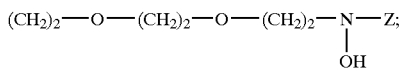

$R_{11}$ is H, OH, O-acyl of 1–4 carbons or O-alkyl of 1–4 carbons or $R_{11}$ is part of a fused ring system when $R_6$ is —C=C—C=C—;

A is CH or C(OH);

B is S, O, N or $CH_2$;

n is 0 or 1;

p is 0, 1 or 2; and

Z is

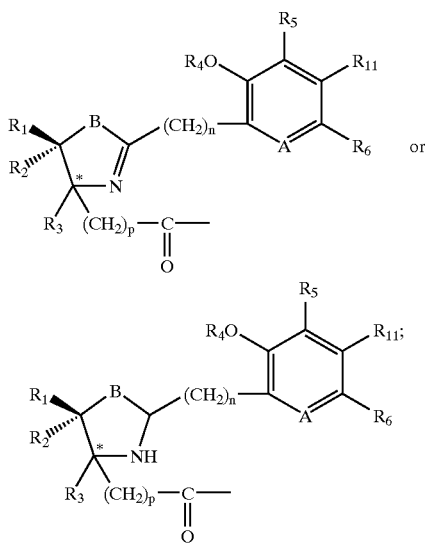

wherein each of the substituents shown is defined above,
or a pharmaceutically acceptable salt of the compound represented by formula (I) or (V) or a stereoisomer of the compound or mixture of stereoisomers.

15. The composition of claim 14, wherein A is CH.
16. The composition of claim 15, wherein B is S, and n and p each is 0.
17. The composition of claim 15, wherein
each of $R_1$, $R_2$, $R_3$ and $R_4$ is H or $CH_3$,
each of $R_5$ and $R_{11}$, is H, OH, O-acyl of 1–4 carbons or O-alkyl of 1–4 carbons, and
$R_6$ is H, OH, alkyl of 1–6 carbons or a halogen.
18. The composition of claim 17, wherein $R_4$ is H.
19. A pharmaceutical composition comprising a compound represented by formula (I) or (V), in combination with a pharmaceutically acceptable excipient, wherein formulas (I) and (V) are (I)

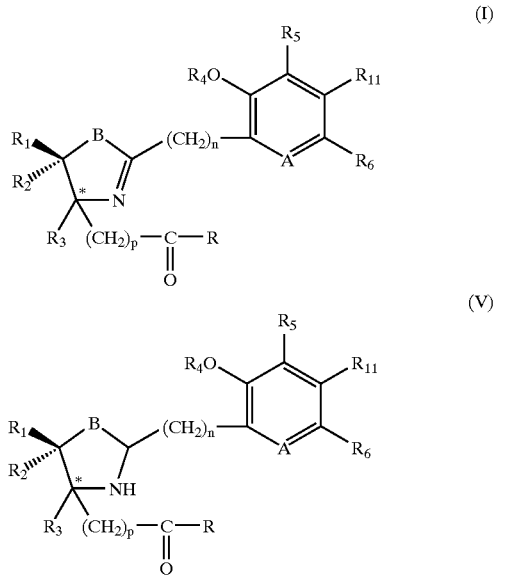

(V)

where:
R is OH, $OR_7$, or $N(OH)R_8$;

$R_1$ is H, $CH_3$ or absent;
$R_2$ is H, $CH_3$ or absent, provided that $R_1$ and $R_2$ are not both absent;
$R_3$ is H or $CH_3$, or $R_3$ is absent when one of $R_1$ or $R_2$ is absent forming a double bond between the $R_1/R_2$ carbon and the $R_3$ carbon;
$R_4$ is H, acyl of 1–4 carbons or alkyl of 1–4 carbons;
$R_5$ is H, OH, O-acyl of 1–4 carbons or O-alkyl of 1–4 carbons;
$R_6$ is $(CH_2)_a R_{10}(CH_2)_r R_{10}Y$;
$R_7$ is alkyl of one to four carbons or optionally substituted benzyl;
$R_8$ is H, alkyl of one to four carbons, optionally, substituted benzyl, or

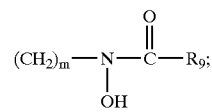

$R_9$ is H, alkyl of one to four carbons or optionally substituted benzyl;
$R_{10}$ is O or $CH_2$;
$R_{11}$ is H, OH, O-acyl of 1–4 carbons or O-alkyl of 1–4 carbons;
A is CH or C(OH);
B is S, O, N or $CH_2$;
a is 2 or 3;
m is an integer from 1 to 8;
n is 0 or 1;
p is 0, 1 or 2;
r is 2 or 3; and
Y is

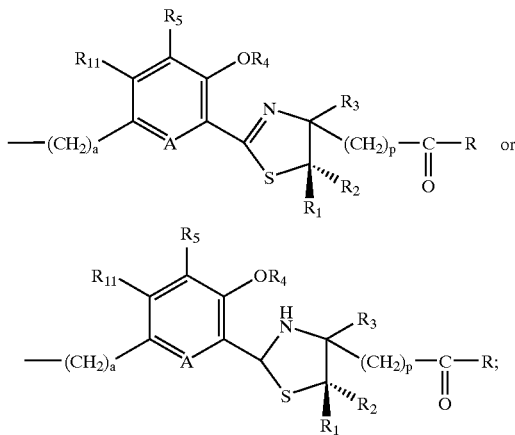

wherein each of the substituents shown is defined above,
or a pharmaceutically acceptable salt of the compound represented by formula (I) or (V) or a stereoisomer of the compound or mixture of stereoisomers.

20. The composition of claim 19, wherein A is CH.
21. The composition of claim 20, wherein B is S, and n and p each is 0.
22. The composition of claim 21, wherein $R_4$ is H.
23. The composition of claim 22, wherein R is $N(OH)R_8$.
24. The composition of claim 22, wherein $R_{11}$ is OH and each of $R_1$ and $R_2$ is H.

25. The composition of claim 24, wherein a is 3, and each of $R_3$ and $R_5$ is H.

26. The composition of claim 25, wherein $R_{10}$ is $CH_2$ and r is 2.

27. The composition of claim 25, wherein $R_{10}$ is $CH_2$ and r is 3.

28. The composition of claim 25, wherein $R_{10}$ is O and r is 2.

29. The composition of claim 25, wherein $R_{10}$ is O and r is 3.

30. The composition of claim 3, wherein R is $N(OH)R_8$.

31. The composition of claim 23, wherein $R_{11}$ is OH and each of $R_1$ and $R_2$ H.

32. The composition of claim 31, wherein a is 3 and each of $R_3$ and $R_5$ is H.

33. The composition of claim 32, wherein $R_8$ is $CH_3$, $R_{10}$ is O and r is 3.

34. The composition of claim 18, wherein $R_{11}$ is OH.

35. The composition of claim 34, wherein each of $R_1$ and $R_2$ is H.

36. The composition of claim 35, wherein each of $R_3$, $R_5$ and $R_6$ is H.

37. A compound of the formula:

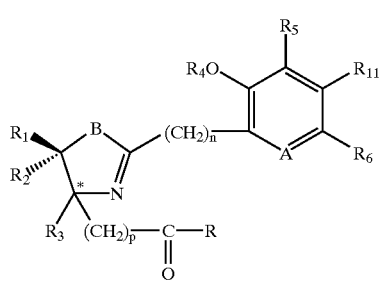
(I)

wherein:

R is $N(OH)R_8$;

each of $R_1$, $R_2$ and $R_3$ is H or $CH_3$;

$R_4$ is H, acyl of 1–4 carbons or alkyl of 1–4 carbons;

$R_5$ is H, OH, O-acyl of 1–4 carbons or O-alkyl of 1–4 carbons;

$R_6$ is H, OH, alkyl of 1–6 carbons or halogen;

$R_8$ is

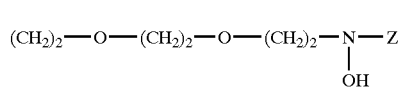

$R_{11}$ is H, OH, O-acyl of 1–4 carbons or O-alkyl of 1–4 carbons;

A is CH;

B is S, O, N or $CH_2$;

n and p each is 0;

z is

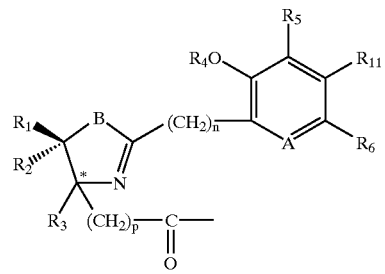
(I)

wherein each of the substitutes shown is described above, or a pharmaceutically-acceptable salt of the compound of formula (I) or a stereoisomer of the compound or mixture of stereoisomers.

38. The compound of claim 37, wherein A is CH and B is S.

39. The compound of claim 38, wherein $R_4$ is H.

40. The compound of claim 39, wherein each of $R_1$ and $R_2$ is H.

41. The compound of claim 40, wherein $R_{11}$ is OH, and each of $R_3$, $R_5$ and $R_6$ is H.

42. A compound of the formula:

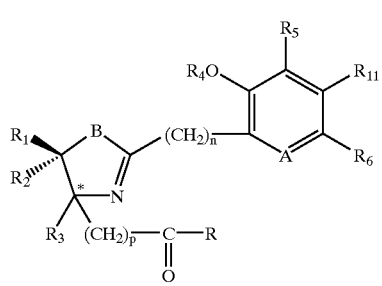
(I)

wherein:

R is OH or $N(OH)R_8$;

each of $R_1$, $R_2$ and $R_3$ is H or $CH_3$;

$R_4$ is H, acyl of 1–4 carbons or alkyl of 1–4 carbons;

$R_5$ is $((CH_2)_a(R_{10}))_b(CH_2)_aR_{10}((CH_2)_a(R_{10}))_bX$;

$R_6$ is H, OH, alkyl of 1–6 carbons or halogen;

$R_8$ is H, alkyl of 1–4 carbons, optionally substituted benzyl or $(CH_2)_mN(OH)C(O)R_9$;

$R_9$ is H, alkyl of 1–4 carbons or optionally substituted benzyl;

$R_{10}$ is O or $CH_2$;

$R_{11}$ is H, OH, O-acyl of 1–4 carbons or O-alkyl of 1–4 carbons;

A is CH;

B is S, O, N or $CH_2$;

a is 2 or 3;

b is 0 or 1;

n and p each is 0; and

X is

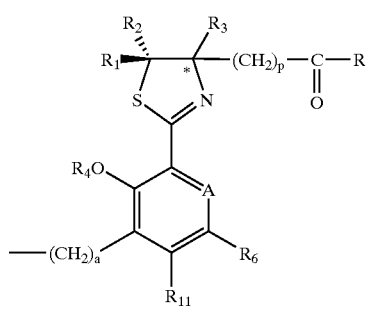

wherein each of the substituents shown is described above,
or a pharmaceutically acceptable salt of the compound of formula (I) or a stereoisomer of the compound or mixture of stereoisomers.

43. The compound of claim 42, wherein A is CH and B is S.

44. The compound of claim 43, wherein $R_4$ is H, each of R and $R_{11}$ is OH, and each of $R_1$ and $R_2$ is H.

45. The compound of claim 44, wherein a is 2 and $R_3$ and $R_6$ are H.

46. The compound of claim 45, wherein $R_{10}$ is $CH_2$ and b is 0.

47. The compound of claim 45, wherein $R_{10}$ is $CH_2$ and b is 1.

48. The compound of claim 45, wherein $R_{10}$ is O and b is 0.

49. The compound of claim 45, wherein $R_{10}$ is O and b is 1.

50. A compound of the formula:

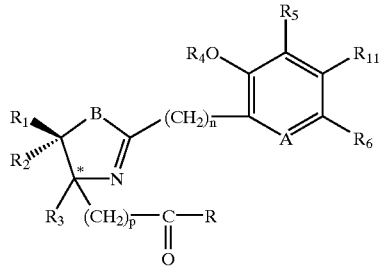

wherein:
R is OH or $N(OH)R_8$;
each of $R_1$, $R_2$ and $R_3$ is H or $CH_3$;
$R_4$ is H, acyl of 1–4 carbons or alkyl of 1–4 carbons;
$R_5$ is H, OH, O-acyl of 1–4 carbons or O-alkyl of 1–4 carbons;
$R_6$ is $(CH_2)_a R_{10}(CH_2)_r R_{10} Y$;
$R_8$ is H, alkyl of 1–4 carbons, optionally substituted benzyl or $(CH_2)_m N(OH)C(OH)R_9$;
$R_9$ is H, alkyl of 1–4 carbons, or optionally substituted benzyl;
$R_{10}$ is O or $CH_2$;
$R_{11}$ is H, OH, O-acyl of 1–4 carbons or O-alkyl of 1–4 carbons;
A is CH;
B is S, O, N or $CH_2$;
a is 2 or 3;
n and p each is 0;
r is 2 or 3;
Y is

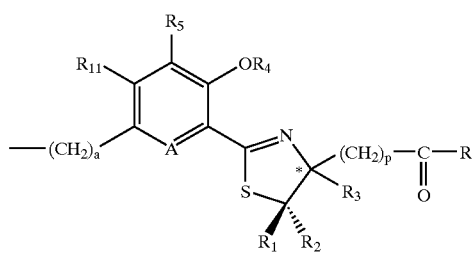

wherein each of the substituents shown is described above,
or a pharmaceutically acceptable salt of the compound of formula (I) or a stereoisomer of the compound or a mixture of stereoisomers.

51. The compound of claim 50, wherein A is CH and B is S.

52. The compound of claim 51, wherein a is 3, each of $R_1$, $R_2$, $R_3$, $R_4$ and $R_5$ is H, and each of R and $R_{11}$ is OH.

53. The compound of claim 52, wherein $R_{10}$ is $CH_2$ and r is 2.

54. The compound of claim 52, wherein $R_{10}$ is $CH_2$ and r is 3.

55. The compound of claim 52, wherein $R_{10}$ is O and r is 2.

56. The compound of claim 52, wherein $R_{10}$ is O and r is 3.

57. A compound of the formula:

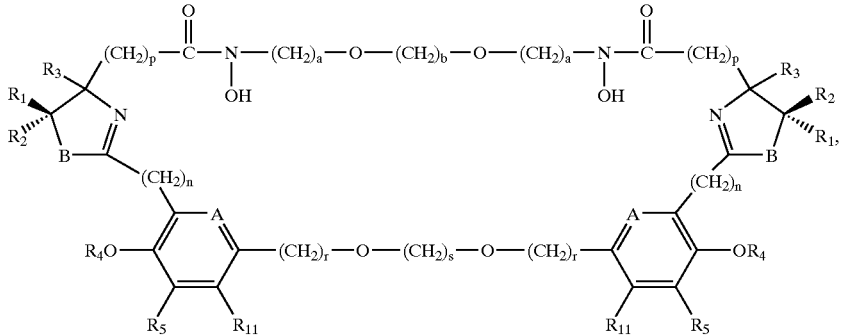

wherein:
$R_1$ is H or $CH_3$;

$R_2$ is H or $CH_3$;
$R_3$ is H or $CH_3$;
$R_4$ is H, acyl of 1–4 carbons or alkyl of 1–4 carbons;
$R_5$ is H, OH, O-acyl of 1–4 carbons or O-alkyl of 1–4 carbons;
$R_{11}$ is H, OH, O-acyl of 1–4 carbons or O-alkyl of 1–4 carbons;
A is CH;
B is S, O, N or $CH_2$;
a is 1, 2 or 3;
b is an integer from 2 to 8;
n is 0 or 1;
p is 0, 1 or 2;
r is 1, 2 or 3; and
s is 1, 2 or 3, or a pharmaceutically acceptable salt of the compound or a stereoisomer of the compound or a mixture of stereoisomers.

58. The compound of claim 57, wherein A is CH.

59. The compound of claim 58, wherein B is S.

60. The compound of claim 59, wherein $R_4$ is H.

61. The compound of claim 60, wherein $R_{11}$ is OH, $R_1$, $R_2$ and $R_5$ are H, and n and p are 0.

62. The compound of claim 61, wherein r and s are 3, a is 2, and b is 2.

* * * * *

UNITED STATES PATENT AND TRADEMARK OFFICE
CERTIFICATE OF CORRECTION

PATENT NO. : 6,864,270 B2
DATED : March 8, 2005
INVENTOR(S) : Raymond J. Bergeron, Jr.

It is certified that error appears in the above-identified patent and that said Letters Patent is hereby corrected as shown below:

<u>Column 38,</u>
Line 62, delete "tour" and insert -- four --.

Signed and Sealed this

Twenty-third Day of August, 2005

JON W. DUDAS
*Director of the United States Patent and Trademark Office*